(12) United States Patent
Ng

(10) Patent No.: US 11,731,886 B2
(45) Date of Patent: Aug. 22, 2023

(54) SYSTEMS, DEVICES, AND METHODS FOR SANITIZING STORED CONTENTS

(71) Applicant: Casetagram Limited, Kowloon (HK)

(72) Inventor: Pui Sun Wesley Ng, Kowloon (HK)

(73) Assignee: Casetagram Limited, Kowloon (HK)

( * ) Notice: Subject to any disclaimer, the term of this patent is extended or adjusted under 35 U.S.C. 154(b) by 218 days.

(21) Appl. No.: 17/107,595

(22) Filed: Nov. 30, 2020

(65) Prior Publication Data

US 2022/0169539 A1 Jun. 2, 2022

(51) Int. Cl.
  *C02F 1/32* (2023.01)
  *A61L 2/10* (2006.01)
  *A61L 2/24* (2006.01)
  *C02F 1/00* (2023.01)

(52) U.S. Cl.
  CPC ............... *C02F 1/325* (2013.01); *A61L 2/10* (2013.01); *A61L 2/24* (2013.01); *C02F 1/008* (2013.01);
  (Continued)

(58) Field of Classification Search
  CPC .... C02F 1/325; C02F 1/08; C02F 2201/3227; C02F 2201/36; C02F 2209/03;
  (Continued)

(56) References Cited

U.S. PATENT DOCUMENTS

2010/0206787 A1* 8/2010 Rozenberg ............. G01N 21/33
  210/96.1
2020/0331755 A1* 10/2020 Odame-Ankrah ..... B01J 19/126
  (Continued)

FOREIGN PATENT DOCUMENTS

CN 203461291 U 3/2014
CN 104340508 A 2/2015
  (Continued)

OTHER PUBLICATIONS

First Office Action and search report issued in PRC application No. 202110443726.2., dated Jun. 21, 2022.

*Primary Examiner* — Nicole M Ippolito
(74) *Attorney, Agent, or Firm* — Baker & McKenzie LLP

(57) ABSTRACT

Embodiments relate to systems, devices, and methods for sanitizing stored contents. System includes main and secondary assemblies. Main assembly includes main opening and main storage section. Secondary assembly includes securing portion, radiation assembly, and control assembly. Securing portion transitions between secured and unsecured states. Secured state is when main and secondary assemblies are secured together. Radiation assembly is configured to emit radiation, and is formed symmetrically relative to a central axis. Control assembly includes first and second safety assemblies and control processor. First safety assembly is configured to determine whether the storage system is in the secured or unsecured state. Second safety assembly is configured to determine whether the secondary assembly is in a safe or unsafe orientation state. Control processor is configured to control the radiation assembly to emit radiation when the storage system is in the secured state and the secondary assembly is in the safe orientation state.

36 Claims, 9 Drawing Sheets

(52) U.S. Cl.
CPC ...... *A61L 2202/11* (2013.01); *A61L 2202/121* (2013.01); *A61L 2202/122* (2013.01); *A61L 2202/14* (2013.01); *A61L 2202/182* (2013.01); *C02F 2201/326* (2013.01); *C02F 2201/3227* (2013.01); *C02F 2209/03* (2013.01); *C02F 2303/04* (2013.01)

(58) Field of Classification Search
CPC .......... C02F 2303/04; A61L 2/10; A61L 2/24; A61L 2202/11; A61L 2202/121; A61L 2202/122; A61L 2202/14; A61L 2202/182
USPC ...................................................... 250/423 R
See application file for complete search history.

(56) References Cited

U.S. PATENT DOCUMENTS

| | | | | |
|---|---|---|---|---|
| 2020/0331775 A1* | 10/2020 | Schowalter | ............... | A61L 2/10 |
| 2021/0299316 A1* | 9/2021 | Mullen | ................... | A61L 2/26 |
| 2022/0176336 A1* | 6/2022 | Taghipour | ............ | B01J 19/0053 |
| 2022/0211890 A1* | 7/2022 | Duck | ....................... | A61L 2/10 |

FOREIGN PATENT DOCUMENTS

| | | |
|---|---|---|
| CN | 204324122 U | 5/2015 |
| CN | 106942968 A | 7/2017 |
| CN | 207574971 U | 7/2018 |
| CN | 108497862 A | 9/2018 |
| CN | 208784273 U | 4/2019 |
| CN | 110025796 A | 7/2019 |
| KR | 20110035384 A | 4/2011 |

\* cited by examiner

SYSTEMS, DEVICES, AND METHODS FOR SANITIZING STORED CONTENTS

TECHNICAL FIELD

The present disclosure relates generally to storage system, and more specifically, to storage systems for use in storing contents and safely sanitizing of contents stored in the storage system.

BACKGROUND

Diseases and/or other medical conditions caused by viruses, bacteria, and/or other infectious agents have become increasingly problematic over the years, with the past year or so demonstrating just how devastating and disastrous infectious diseases can be to all aspects of our lives. In an attempt to combat quick-spreading diseases caused by viruses, bacteria, and/or other infectious agents, several initiatives, recommendations and best practices have been issued and adopted including, but not limited to, improving personal hygiene and cleanliness (e.g., more frequent and diligent hand washing, wearing of masks in public, reducing of public touchpoints, use of personal portable water/consumable containers to reduce exposure to potential viruses, bacteria, and/or other infectious agents, etc.).

BRIEF SUMMARY

With the increasingly prevalent and quick-spreading occurrences of infectious diseases caused by viruses, bacteria, and/or other infectious agents, there is an ever-growing need to be safe and clean, and to sanitize and/or disinfect the things we touch and/or consume. Personal portable storage containers, such as refillable/reusable water bottles, food containers, or the like, have become an all-around smart solution globally, one that not only reduces the risks of being exposed to contaminated containers and/or consumables from others (e.g., stores, restaurants, etc.) but also reduces waste/garbage (e.g., as compared to single-use containers). While such storage containers indeed enable users to portably carry around and have ready/easy access to consumables (e.g., water, soup, food, etc.) and non-consumables (e.g., utensils, etc.), it is recognized in the present disclosure that the storage sections of such storage containers and/or the stored contents themselves (e.g., water, other liquids, food, utensils, etc.) may be contaminated and/or receive, carry, culture, grow, and/or attract viruses, bacteria, and/or other infectious agents, and as a result may cause users of such storage containers to become sick and/or infected when such consumables are consumed.

Recent studies have shown that certain forms of radiation, energy, light, emissions, or the like (referred to herein as "radiation", "UV radiation", "UV light", or the like), such as ultraviolet (UV) light (and more specifically, ultraviolet-C (UV-C) light), can be effective at inactivating various forms of viruses (and/or bacteria and/or other infectious agents) including, but not limited to, the severe acute respiratory syndrome coronavirus 2, or SARS-CoV-2 (or COVID-19), by destroying the outer protein coating of the virus. While such radiation may indeed be useful for sanitizing and/or disinfecting consumables and/or non-consumables against viruses, bacteria, and/or other infectious agents, such radiation can also be harmful to users (e.g., when such radiation is emitted or irradiated into a user's eye(s) and/or skin).

The present disclosure relates generally to systems, devices, and methods for sanitizing or disinfecting contents stored in a storage system. More specifically, the present disclosure relates to the selective and/or safe use or application of radiation (e.g., UV radiation) to sanitize and/or disinfect contents stored in a storage system, while ensuring that such radiation is transmitted, emitted or irradiated in a manner that is safe to the user of the storage system and/or those nearby (e.g., reduction or elimination of risks of emitting or irradiating the radiation into the eye(s) of the user and/or persons nearby the storage system).

In an exemplary embodiment, a storage system is described. The storage system includes a main assembly and secondary assembly. The main assembly includes a main opening and main storage section configured to receive a liquid via the main opening. The secondary assembly includes a securing portion, radiation assembly, and control assembly. The securing portion is transitionable between a secured state and unsecured state. The secured state is a state in which the main assembly and secondary assembly are secured together via the securing portion. The unsecured state is a state in which the main assembly and secondary assembly are not secured together. The radiation assembly is configured to emit UV radiation. The radiation assembly is formed symmetrically relative to a first central axis. The control assembly includes a first safety assembly, second safety assembly, and control processor. The first safety assembly is configured to determine whether the storage system is in the secured or unsecured state. The second safety assembly is configured to determine whether the secondary assembly is in a safe or unsafe orientation state. The control processor is configured to control the radiation assembly to emit the UV radiation when the first safety assembly determines that the storage system is in the secured state and the second safety assembly determines that the secondary assembly is in the safe orientation state.

In another exemplary embodiment, a storage system is described. The storage system includes a main assembly and secondary assembly. The main assembly includes a main opening, main securing portion, and main storage section formed by a surrounding side wall and a bottom wall opposite to the main opening. The main storage section is configured to receive a liquid via the main opening. The secondary assembly is configured to secure to and unsecure from the main assembly. The secondary assembly includes a secondary securing portion, radiation assembly, and control assembly. The secondary securing portion is configured to cooperate with the main securing portion to transition the liquid storage system between a secured state and an unsecured state. The secured state is a state in which the secondary securing portion and the main securing portion are secured together to create a secure hermetical seal of the main opening. The unsecured state is a state in which the secondary securing portion and the main securing portion are not secured together to create a secure hermetical seal of the main opening. The radiation assembly is configured to emit radiation. The radiation assembly is formed symmetrically relative to a first central axis. The control assembly includes a first safety assembly, second safety assembly, and control processor. The first safety assembly is configured to determine whether the liquid storage system is in the secured state or the unsecured state. The second safety assembly is configured to determine whether the secondary assembly is in: a safe orientation, the safe orientation state being a state in which an orientation of the radiation assembly relative to a zero-slope vertical axis satisfies the following condition: an absolute value of an angular difference between the first central axis of the radiation assembly and the zero-slope vertical axis is less than or equal to a first predetermined threshold; or an unsafe orientation, the unsafe orientation state being a state in which the orientation of the radiation assembly relative to the zero-slope vertical axis satisfies the following condition: the absolute value of the angular difference between the first central axis of the radiation assembly and the zero-slope vertical axis is greater than the first predetermined threshold. The control processor is configured to control the radiation assembly to emit the UV radiation when the first safety assembly determines that the liquid storage system is in the secured state and the second safety assembly determines that the secondary assembly is in the safe orientation state.

In another exemplary embodiment, a storage system is described. The storage system includes a main assembly and a secondary assembly. The main assembly includes a main opening, main securing portion, and main storage section formed by a surrounding side wall and a bottom wall opposite to the main opening. The main storage section is configured to receive a liquid via the main opening. The secondary assembly is configured to secure to and unsecure from the main assembly. The secondary assembly includes a secondary securing portion, radiation assembly, and control assembly. The secondary securing portion is configured to cooperate with the main securing portion to transition the liquid storage system between a secured state and an unsecured state. The secured state is a state in which the secondary securing portion and the main securing portion are secured together to hermetically seal the main opening. The unsecured state is a state in which the secondary securing portion and the main securing portion are not secured together to hermetically seal the main opening. The radiation assembly is configured to emit UV radiation. The radiation assembly is formed symmetrically relative to a first central axis. The control assembly includes a first safety assembly, second safety assembly, and control processor. The first safety assembly is configured to determine whether the liquid storage system is in the secured state or the unsecured state. The second safety assembly is configured to determine whether the secondary assembly is in a safe orientation state or an unsafe orientation state. The control processor is configured to: control the radiation assembly to emit the UV radiation when the first safety assembly determines that the liquid storage system is in the secured state and the second safety assembly determines that the secondary assembly is in the safe orientation state; control the radiation assembly to not emit the UV radiation when the first safety assembly determines that the liquid storage system is in the secured state and the second safety assembly determines that the secondary assembly is in the unsafe orientation state (or not control the radiation assembly to emit the UV radiation when the first safety assembly determines that the liquid storage system is in the secured state and the second safety assembly determines that the secondary assembly is in the unsafe orientation state); control the radiation assembly to not emit the UV radiation when the first safety assembly determines that the liquid storage system is in the unsecured state and the second safety assembly determines that the secondary assembly is in the safe orientation state (or not control the radiation assembly to emit the UV radiation when the first safety assembly determines that the liquid storage system is in the unsecured state and the second safety assembly determines that the secondary assembly is in the safe orientation state); and control the radiation assembly to not emit the UV radiation when the first safety assembly determines that the liquid storage system is in the unsecured state and the second safety assembly determines that the secondary assembly is in the unsafe orientation state (or not control the radiation assembly to emit the UV radiation when the first safety assembly determines that the liquid storage system is in the unsecured state and the second safety assembly determines that the secondary assembly is in the unsafe orientation state).

BRIEF DESCRIPTION OF THE FIGURES

For a more complete understanding of the present disclosure, example embodiments, and their advantages, reference is now made to the following description taken in conjunction with the accompanying figures, in which like reference numbers indicate like features, and.

Although similar reference numbers may be used to refer to similar elements in the figures for convenience, it can be appreciated that each of the various example embodiments may be considered to be distinct variations.

Figure 1A:
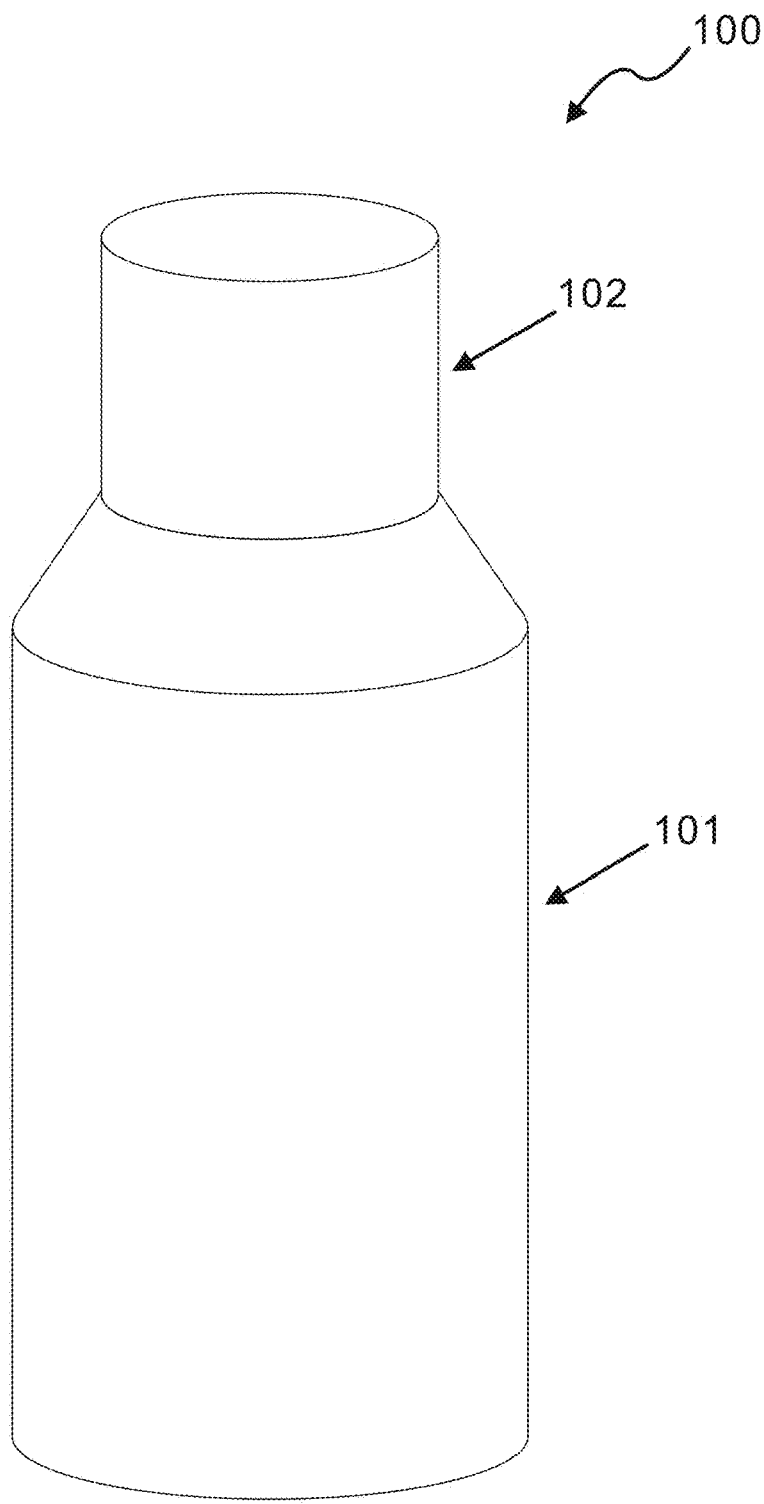
FIG. 1A illustrates a perspective view of an example embodiment of the storage assembly in a secured state, with the main assembly secured to the secondary assembly.

Example embodiments will now be described with reference to the accompanying figures, which form a part of the present disclosure and which illustrate example embodiments which may be practiced. As used in the present disclosure and the appended claims, the terms "embodiment," "example embodiment," "exemplary embodiment," and "present embodiment" do not necessarily refer to a single embodiment, although they may, and various example embodiments may be readily combined and/or interchanged without departing from the scope or spirit of example embodiments. Furthermore, the terminology as used in the present disclosure and the appended claims is for the purpose of describing example embodiments only and is not intended to be limitations. In this respect, as used in the present disclosure and the appended claims, the term "in" may include "in" and "on," and the terms "a," "an," and "the" may include singular and plural references. Furthermore, as used in the present disclosure and the appended claims, the term "by" may also mean "from," depending on the context. Furthermore, as used in the present disclosure and the appended claims, the term "if" may also mean "when" or "upon," depending on the context. Furthermore, as used in the present disclosure and appended claims, the words "and/or" may refer to and encompass any or all possible combinations of one or more of the associated listed items.

DETAILED DESCRIPTION

There is an ever-growing need to improve personal hygiene, and to sanitize and/or disinfect the things we touch and/or consume. The use of personal portable storage containers, such as refillable/reusable water bottles, or the like, may assist in reducing risks of exposure to viruses, bacteria, and/or other infectious agents as compared to single-use containers. While such storage containers indeed enable users to portably carry around and have ready/easy access to consumables (e.g., water, soup, food, etc.) and non-consumables (e.g., utensils, etc.), it is recognized in the present disclosure that the storage sections of such storage containers and/or the stored contents themselves may be contaminated and/or receive, carry, culture, grow, and/or attract viruses, bacteria, and/or other infectious agents, and as a result may cause users of such storage containers to become sick and/or infected when such consumables are consumed.

Present example embodiments relate generally to and/or include systems, subsystems, processors, devices, logic, methods, and processes for addressing conventional problems, including those described above and in the present disclosure, and more specifically, example embodiments relate to systems, subsystems, processors, devices, logic, methods, and processes for storing contents and for sanitizing or disinfecting of contents stored in a storage system.

It is to be understood that, while example embodiments are mostly described in the present disclosure as pertaining to liquid storage systems such as portable liquid containers and water bottles, the principles described in the present disclosure may also be applied beyond the context of liquid bottles, such as for use with food containers, kettles, tea pots, coffee dispensers, etc., without departing from the teachings of the present disclosure.

Example embodiments will now be described below with reference to the accompanying figures, which form a part of the present disclosure.

Example Embodiments of a Storage System (e.g., System 100)

Figure 1B:
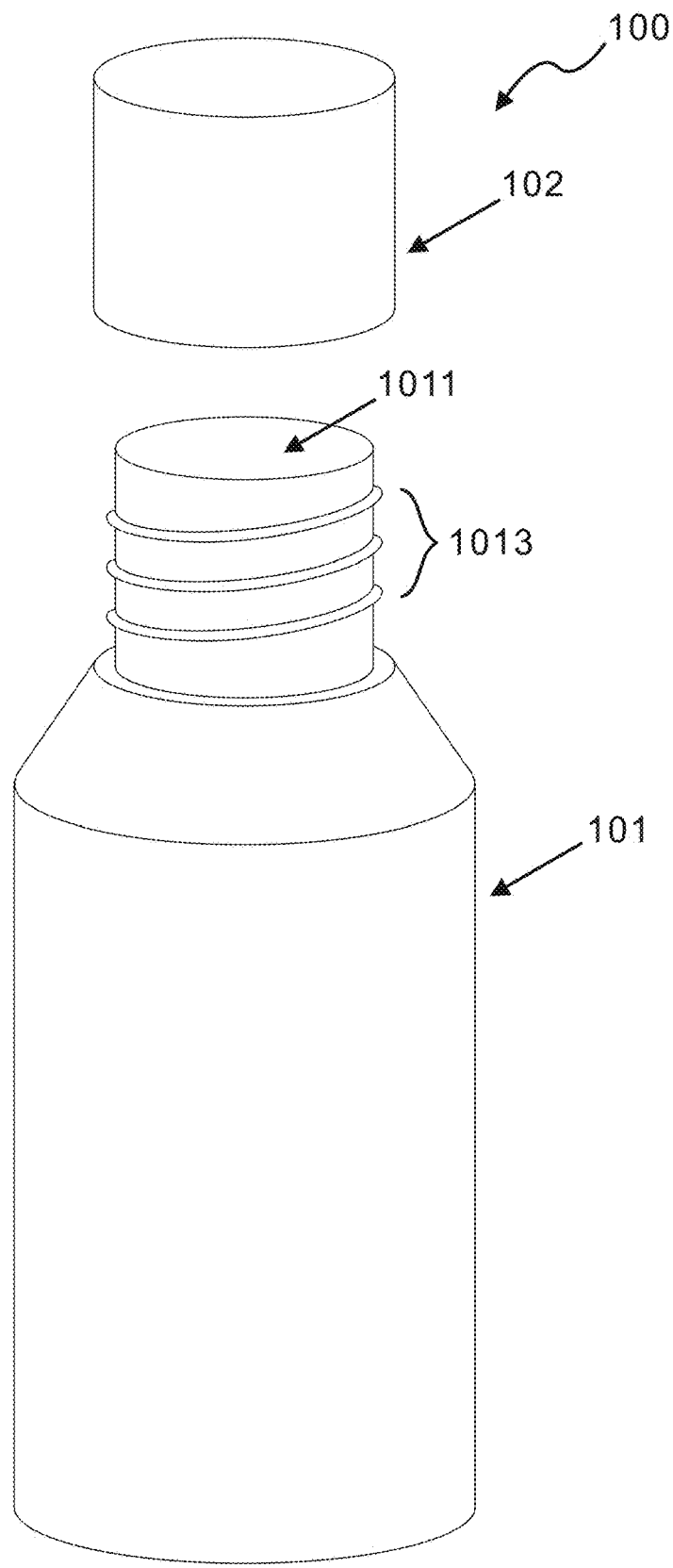
FIG. 1B illustrates a perspective view of an example embodiment of the storage assembly in an unsecured state, with the main assembly unsecured from the secondary assembly.

FIGS. 1A and 1B illustrate an example embodiment of a storage system (e.g., storage system 100). The storage system 100 includes a main assembly (e.g., main assembly 101) and a secondary assembly (e.g., secondary assembly 102).

In example embodiments, the main assembly 101 may include, resemble, and/or be formed as a bottle, container, or the like. As will be further described in the present disclosure, the main assembly 101 may include a main opening (e.g., main opening 1011) for receiving and discharging contents, such as liquids, solids, or the like. The main assembly 101 may also include a main storage section (e.g., main storage section 1012) for storing contents, such as liquids, solids, or the like, received via the main opening 1011.

In example embodiments, the secondary assembly 102 may include, resemble, and/or be formed as a cap, lip, cover, top portion, or the like, for a bottle, container, or the like. As will be further described in the present disclosure, the secondary assembly 102 may include a radiation assembly (e.g., radiation assembly 1022) for emitting radiation (e.g., ultraviolet (UV) radiation, etc.). The radiation assembly 1022 itself may include one or more radiation sources 1022 (e.g., UV LED light sources, etc.). The secondary assembly 102 may also include a control assembly (e.g., control assembly 1023) for selectively controlling the radiation assembly 1022 to emit or not emit radiation.

The storage system 100 is configurable or configured to store contents, such as liquids, solids, gases, or the like (referred to herein as "contents", or the like). Such contents may include, but are not limited to, water, other liquids or beverages, soup, food items, medicines, nutritional products, other consumables, non-consumables (e.g., utensils, etc.), one or more gases, and/or a combination of one or more of the aforementioned items. As will be further described in the present disclosure, the storage system 100 may also be configurable or configured to perform a sanitization, disinfection, cleaning, de-contamination, preservation, or the like, (referred to herein as "sanitization", "sanitizing", "disinfection", or "disinfecting") of the main storage section 1012 (including the side interior walls and/or bottom wall forming the main storage section 1012) and/or one or more contents stored in (or housed by) the main storage section 1012. It is to be understood in the present disclosure that the main storage section 1012 may be formed in any shape and/or size including, but not limited to, a cylindrical shape, rectangular shape, combinations of shapes, etc.

To prevent or protect contents stored in the main storage section 1012 from undesirably leaking out from the storage system 100, the storage system 100 may be configurable or configured to provide a secured and/or sealed storage and/or housing of the contents. In example embodiments, such secured and/or sealed storage and/or housing of the contents may be achievable or achieved by a cooperation of one or more elements, parts, sections, and/or portions of the main assembly 101 with one or more elements, parts, sections, and/or portions of the secondary assembly 102. Furthermore, such secured and/or sealed storage and/or housing of the contents may (or may not) provide a hermetic sealing, water-proof sealing, air-tight sealing, or the like, for the storage system 100 (e.g., a hermetic seal, water-proof seal, air-tight seal, or the like, of the main opening 1011 by a portion of the secondary assembly 102).

FIG. 1A illustrates an example state or configuration in which the main assembly 101 (which in this example embodiment is illustrated to resemble a main body of a liquid/water bottle where contents are stored/housed) is secured, connected, and/or attached (referred to herein as "secured") to the secondary assembly 102 (which in this example embodiment is illustrated to resemble a cap, lid, cover, top portion, or the like, for a liquid/water bottle). As used in the present disclosure, such a state or configuration in which the main assembly 101 is secured to the secondary assembly 102 may be referred to as a "secured state", "secured configuration", "sealed state", "sealed configuration", "closed state", "closed configuration", or the like for the storage system 100. It is to be understood that the secured state may be a state in which the main assembly 101 and the secondary assembly 102 are secured together in a hermetically sealed manner (and/or water-proof manner and/or air-tight manner). Alternatively, the secured state may be a state in which the main assembly 101 and the secondary assembly 102 are secured together, but not necessarily in a hermetically sealed manner (or water-proof manner or air-tight manner) (i.e., either the main assembly 101 and the secondary assembly 102 are secured together in a hermetically sealed manner or the main assembly 101 and the secondary assembly 102 are secured together in a non-hermetically sealed manner).

FIG. 1B illustrates an example state or configuration in which the main assembly 101 (which in this example embodiment is illustrated to resemble a main body of a liquid/water bottle where contents are stored/housed) is not secured, connected, and/or attached to (or unsecured, unconnected, and/or unattached from) the secondary assembly 102 (which in this example embodiment is illustrated to resemble a cap, lid, cover, top portion, or the like, for a liquid/water bottle). As used in the present disclosure, such a state or configuration in which the main assembly 101 is unsecured from the secondary assembly 102 (or the main assembly 101 not being secured to the secondary assembly 102) may be referred to as an "unsecured state", "unsecured configuration", "unsealed state", "unsealed configuration", "opened state", "opened configuration", or the like, for the storage system 100. For embodiments of the storage system 100 in which the secured state is a state in which the main assembly 101 and the secondary assembly 102 are secured together in a hermetically sealed manner (and/or water-proof manner and/or air-tight manner), the unsecured state for such storage systems 100 may be any of the following states: a state in which the main assembly 101 and the secondary assembly 102 are secured together, but not in a hermetically sealed manner (or water-proof manner or air-tight manner) (e.g., the main assembly 101 is not fully secured to the secondary assembly 102); or a state in which the main assembly 101 and the secondary assembly 102 are not secured together at all (e.g., the state or configuration illustrated in FIG. 1B). For embodiments of the storage system 100 in which the secured state is a state in which the main assembly 101 and the secondary assembly 102 are secured together, but not necessarily in a hermetically sealed manner (or water-proof manner or air-tight manner) (i.e., may or may not be hermetically sealed), the unsecured state for such storage systems 100 will be a state in which the main assembly 101 and the secondary assembly 102 are not secured together at all (e.g., the state or configuration illustrated in FIG. 1B).

Example embodiments of the storage system 100 and elements thereof will now be further described with reference to the accompanying figures, which form a part of the present disclosure.

The Main Assembly (e.g., Main Assembly 101).

Figure 2A:
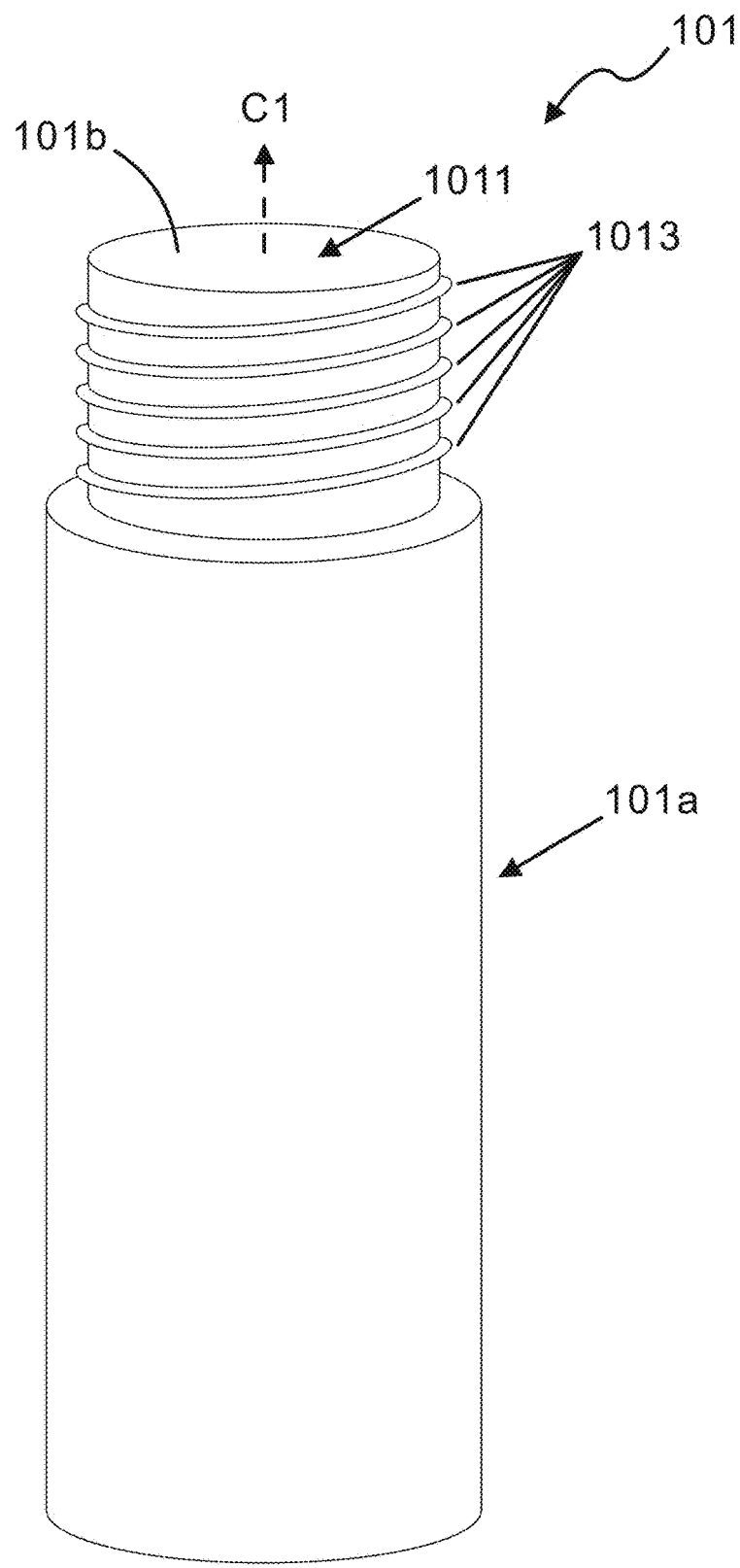
FIG. 2A illustrates a perspective view of an example embodiment of the main assembly.
Figure 2B:
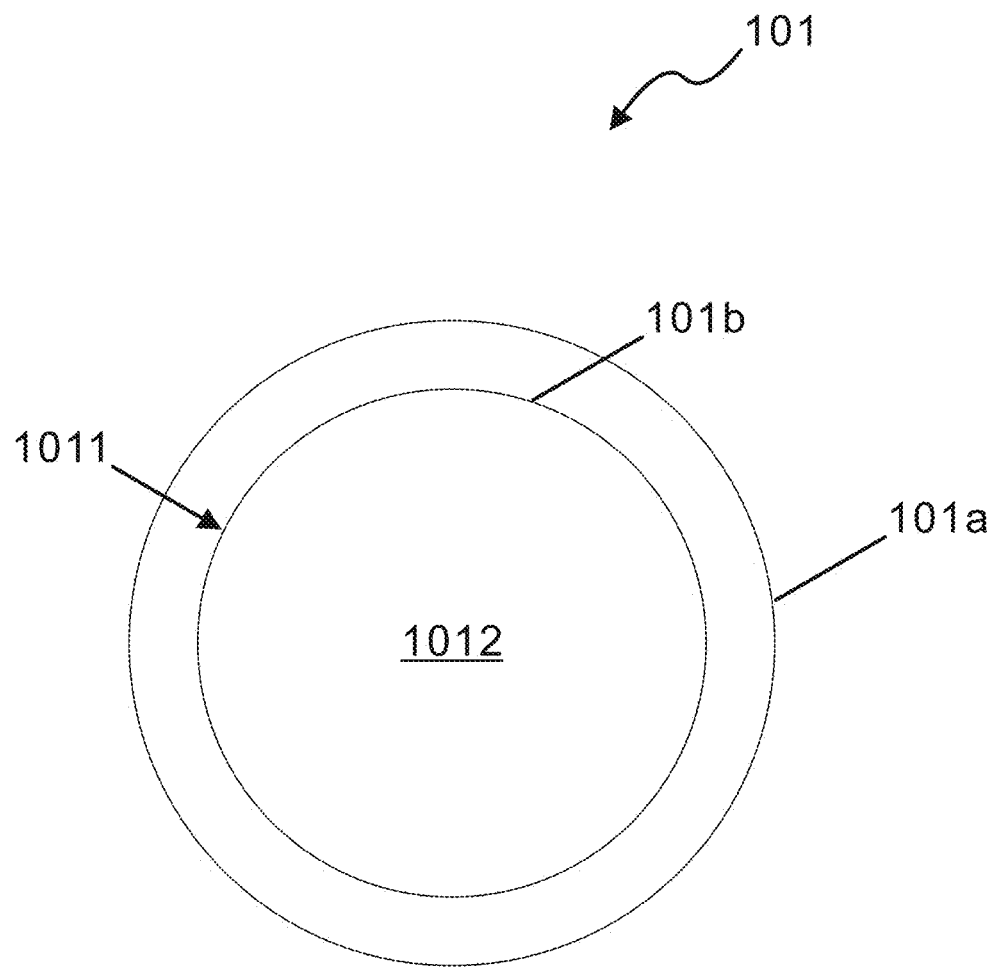
FIG. 2B illustrates a top view of an example embodiment of the main assembly.
Figure 2C:
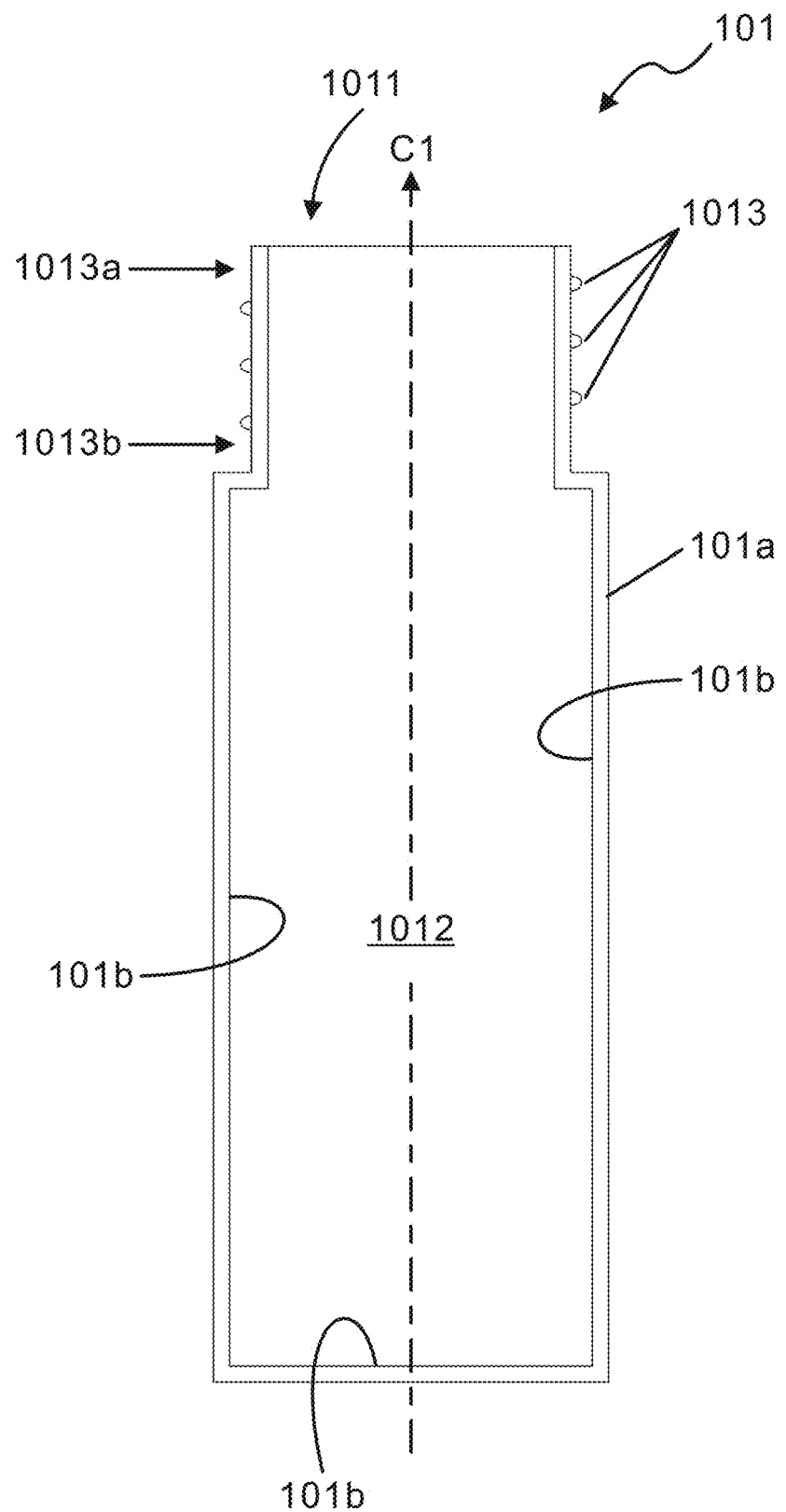
FIG. 2C illustrates a cross-sectional view of an example embodiment of the main assembly.

FIG. 2A, FIG. 2B, and FIG. 2C illustrate a perspective view, top view, and cross-sectional side view, respectively, of an example embodiment of the main assembly (e.g., main assembly 101). The main assembly 101 may include, resemble, and/or be formed as and/or in the shape of a bottle, container, or the like.

As will be further described in the present disclosure, the main assembly 101 may be configurable or configured to secure to and unsecure from an example embodiment of the secondary assembly 102 in a plurality of ways. For example, the storage assembly 100 may include one or more securing portions for securing the main assembly 101 to the secondary assembly 102 (and for unsecuring the main assembly 101 from the secondary assembly 102). As a more specific example, the storage system 100 may include only one securing portion. Alternatively, the storage system 100 may include two or more securing portions (e.g., the storage system 100 may include one or more main securing portions 1013 of the main assembly 101 and one or more secondary securing portions 1021 of the secondary assembly 102). Each securing portion may be configurable or configured to transition between a secured state and an unsecured state; and the one or more securing portions may be configurable or configured to cooperate to transition the storage assembly 100 between a secured state and an unsecured state.

In terms of the secured state of the storage assembly 100, the secured state may be a state in which the main assembly 101 and the secondary assembly 102 are secured together via the one or more securing portions (e.g., securing portion(s) formed on the main assembly 101; securing portion(s) formed on the secondary assembly 102; securing portion(s) formed on both main assembly 101 and secondary assembly 102; or securing portion(s) not formed on either the main assembly 101 or secondary assembly 102, such as securing portion(s) that are and/or become a separate element from the main assembly 101 and the secondary assembly 102 when such securing portion(s) are not used to secure the main assembly 101 and the secondary assembly 102 together). In an example embodiment, the secured state may be a state in which the main assembly 101 and the secondary assembly 102 are secured together in a hermetically sealed manner (and/or water-proof manner and/or air-tight manner) via the one or more securing portions. Alternatively, the secured state may be a state in which the main assembly 101 and the secondary assembly 102 are secured together via the one or more securing portions, but not necessarily secured together in a hermetically sealed manner (or water-proof manner or air-tight manner). Put differently, the secured state in such an example may be either of the following states: a state in which the main assembly 101 and the secondary assembly 102 are either secured together in a hermetically sealed manner via the securing assembly; or a state in which the main assembly 101 and the secondary assembly 102 are either secured together in a non-hermetically sealed manner via the securing assembly).

The unsecured state of the storage assembly 100, on the other hand, may be a state in which the main assembly 101 and the secondary assembly 102 are not secured together via the one or more securing portions (e.g., securing portion(s) as described above and in the present disclosure). For example, in example embodiments where the secured state is a state in which the main assembly 101 and the secondary assembly 102 are secured together in a hermetically sealed manner (and/or water-proof manner and/or air-tight manner) via the one or more securing portions, the unsecured state may be any of the following states: a state in which the main assembly 101 and the secondary assembly 102 are not secured together at all (e.g., the state or configuration illustrated in FIG. 1B); or a state in which the main assembly 101 and the secondary assembly 102 are secured together, but not in a hermetically sealed manner (or water-proof manner or air-tight manner). Alternatively, in example embodiments where the secured state is a state in which the main assembly 101 and the secondary assembly 102 are secured together via the one or more securing portions, but not necessarily secured together in a hermetically sealed manner (or water-proof manner or air-tight manner) (i.e., may or may not be hermetically sealed), the unsecured state for such storage systems 100 will be a state in which the main assembly 101 and the secondary assembly 102 are not secured together at all (e.g., the state or configuration illustrated in FIG. 1B).

As further described below and in the present disclosure, the main assembly 101 may include one or more main storage sections 1012 for storing of contents. The main assembly 101 may also include one or more main openings 1011 for receiving contents into and discharging contents out of the one or more main storage sections 1012. The main assembly 101 may also include an exterior surface 101*a* that forms at least a part of an exterior shape of the main assembly 101. The main assembly 101 may also include an interior surface 101*b* that forms at least a part of the one or more main storage sections 1012. The main assembly 101 may also include one or more securing portions, such as one or more main securing portions 1013. The main assembly 101 may also include on or more other elements (not shown). For example, the main assembly 101 may include a graphical display (not shown), analog indicator, or the like, in communication with the control assembly 1023, radiation assembly 1022, and/or one or more other elements of the storage system 100, for displaying and/or providing an indication of, among other things, one or more of the following: a status of emission of radiation (e.g., by the radiation assembly 1022), signal/power/radiation level/ amount of radiation (e.g., by the radiation assembly 1022), duration of emission of radiation (e.g., by the radiation assembly 1022), sanitization level/amount achieved by applying radiation (e.g., by the radiation assembly 1022), disinfection level/amount achieved by applying radiation (e.g., by the radiation assembly 1022), etc. In example embodiments where the control assembly 1023 (and/or the radiation assembly 1022) are provided in the secondary assembly 102 and the graphical display is provided in the main assembly 101, such communication between the control assembly 1023 (and/or radiation assembly 1022) and the graphical display, analog indicator, or the like, may be provided wirelessly and/or via an electrical connection/path that is established when the main assembly 101 and the secondary assembly 102 are in the secured state. These elements of the main assembly 101 will now be further described below with reference to the accompanying figures, which form a part of the present disclosure.

The Main Opening (e.g., Main Opening 1011).

In an example embodiment, the main assembly 101 may include one or more main openings (e.g., main opening 1011). Each main opening 1011 may be configurable or configured to receive contents, such as liquids, solids, or the like, for storage in the one or more main storage sections 1012. Each main opening 1011 may also be configurable or configured to allow contents stored or housed in the one or more main storage sections 1012 to be removed from, discharged rom, and/or poured out of the main storage section 1012. The main opening 1011 may have and/or be formed symmetrically relative to a central axis C1 (as illustrated in at least FIGS. 2A and 2C).

Although the figures (e.g., FIGS. 1B and 2A-C) illustrate the main assembly 101 as having one main opening 1011 and one main storage section 1012, it is to be understood in the present disclosure that example embodiments of the storage assembly 100 may include more than one main opening 1011 and/or more than one main storage section 1012 without departing from the teachings of the present disclosure.

For example, the main assembly 101 may include two (or more) main openings 1011 and one main storage section 1012. In such an example, the two (or more) main openings 1011 may be for use in receiving contents into the one main storage section 1012. In the same example, the secondary assembly 102 may include a first radiation assembly 1022 for one of the main openings 1011 and a second radiation assembly 1022 for the other main opening 1011 (and one or more other radiation assemblies 1022 if there are more than two main openings 1011). Alternatively, the secondary assembly 102 may include one radiation assembly 1022 (e.g., a radiation assembly 1022 having a plurality radiation sources) configurable or configured to emit radiation through or into the two (or more) main openings 1011. In example embodiments in which the main assembly 101 includes more than two main openings 1011, one main storage section 1012, and more than one radiation assembly 1022, each radiation assembly 1022 may be configurable or configured to emit radiation through or into one or more main openings 1011 (and the number of main opening(s) 1011 receiving radiation from each radiation assembly 1022 may or may not be equal; e.g., a first main opening 1011 may receive radiation from a first radiation assembly 1022 and a second main opening 1011 may receive radiation from a second radiation assembly 1022 and a third radiation assembly 1022; etc.).

As another example, the main assembly 101 may include one main opening 1011 and two (or more) main storage sections 1012. In such an example, the one main opening 1011 may be for use in receiving contents into the two (or more) main storage sections 1012. In the same example, the secondary assembly 102 may include a first radiation assembly 1022 for one (or more) of the main storage sections 1012 and a second radiation assembly 1022 for the other one (or more) main storage section 1012. Alternatively, the secondary assembly 102 may include only one radiation assembly 1022 (e.g., having a plurality radiation sources) configurable or configured to emit radiation into the two (or more) main storage sections 1012. In example embodiments in which the main assembly 101 includes one main opening 1011, more than two main storage section 1012, and more than one radiation assembly 1022, each radiation assembly 1022 may be configurable or configured to emit radiation into one or more main storage sections 1012 (and the number of main storage sections 1012 receiving radiation from each radiation assembly 1022 may or may not be equal; e.g., a first main storage section 1012 may receive radiation from a first radiation assembly 1022 and a second main storage section 1012 may receive radiation from a second radiation assembly 1022 and a third radiation assembly 1022; etc.).

Each of the one or more main openings 1011 may be formed in any one or more shapes and/or sizes including, but not limited to, circular shapes, semi-circular shapes, oval or elliptical shapes, semi-oval or semi-elliptical shapes, square shapes, rectangular shapes, combinations of shapes, etc.

The Main Storage Section (e.g., Main Storage Section 1012).

In an example embodiment, the main assembly 101 may include one or more main storage sections (e.g., main storage section 1012). Each main storage section 1012 may be configurable or configured to receive and store or house contents, such as liquids, solids, or the like, via the one or more main openings 1011. Each main storage section 1012 may also be configurable or configured to allow contents stored or housed in the main storage section 1012 to be removed from, discharged from, and/or poured out of the main storage section 1012. The main storage section 1012 may have and/or be formed symmetrically relative to a central axis C1 (as illustrated in at least FIGS. 2A and 2C).

Although the figures (e.g., FIGS. 1B and 2A-C) illustrate the main assembly 101 as having one main storage section 1012 and one main opening 1011, it is to be understood in the present disclosure that example embodiments of the storage assembly 100 may include more than one main storage section 1012 and/or more than one main opening 1011 without departing from the teachings of the present disclosure.

Each main storage section 1012 may be formed in any one or more shapes and/or sizes including, but not limited to, cylindrical shapes, semi-cylindrical shapes, rectangular shapes, combinations of shapes, etc. Each main storage section 1012 may be formed by one or more interior surfaces 101*b*. For example, when the main storage section 1012 is cylindrical in shape, the interior surfaces 101*b* may include an interior surface 101*b* forming the cylindrical side wall and an interior surface 101b forming the bottom wall, and may also include an interior surface 1012 forming the top wall (which includes the one or more main openings 1011). As another example, when the main storage section 1012 is rectangular in shape, the interior surfaces 101b may include interior surfaces 101b forming the four side walls and an interior surface 101b forming the bottom wall, and may also include an interior surface 1012 forming the top wall (which includes the one or more main openings 1011). Other examples are contemplated without departing from the teachings of the present disclosure.

The Main Securing Portion (e.g., Main Securing Portion 1013).

In an example embodiment, the main assembly 101 may include one or more main securing portions (e.g., main securing portion 1013). The one or more main securing portions 1013 may be configurable or configured to secure the main assembly 101 to the secondary assembly 102 (and unsecure the main assembly 101 from the secondary assembly 102). The one or more main securing portions 1013 may be configurable or configured to be transitioned between a secured state (which may correspond to a state in which the main securing portion 1013 is secured to a corresponding secondary securing portion 1021) and an unsecured state (which may correspond to a state in which the main securing portion 1013 is unsecured from a corresponding secondary securing portion 1021). Alternatively or in addition, the one or more main securing portions 1013 may be configurable or configured to transition the storage assembly 100 between the secured state and the unsecured state (as described in the present disclosure).

The main securing portion 1013 may be formed in one or of a plurality of configurations. For example, the main securing portion 1013 may be formed or provided as a threaded portion, such as those found in a threaded bottle top, threaded bottle top funnel, screw cap, or the like, on an exterior surface 101a portion of the main assembly 101, in which case the secondary assembly 102 may also include a secondary securing portion 1021 having a complimentary or corresponding threaded portion on an interior surface 102b of the secondary assembly 102 for receiving the threaded portion(s) of the main securing portion 1013. Alternatively, the main securing portion 1013 may be formed or provided as a threaded portion on an interior surface 101b portion of the main assembly 101 (e.g., in the neck portion, main opening 1011, and/or main storage section 1012 of the main assembly 101), in which case the secondary assembly 102 may also include a secondary securing portion 1021 having a complimentary or corresponding threaded portion on an exterior surface 102a of the secondary assembly 102 for receiving the threaded portion(s) of the main securing portion 1013. FIGS. 1B, 2A, and 2C illustrate example embodiments of the main securing portion 1013 having such threaded portions.

Alternatively or in addition, the main securing portion 1013 may be formed or provided as a push-button lock/unlock, latch lock/unlock, and/or any other securing/unsecuring configuration or mechanism without departing from the teachings of the present disclosure. In such embodiments, the secondary assembly 102 may also include a secondary securing portion 1021 formed or provided having a complimentary configuration or mechanism as the main securing portion 1013. It is to be understood in the present disclosure that the storage assembly 100 may also have a single securing portion (1013 and/or 1021) configurable or configured to secure the main assembly 101 to the secondary assembly 102 and configurable or configured to transition the storage assembly 100 between the secured state and the unsecured state (as described in the present disclosure) without departing from the teachings of the present disclosure.

The Secondary Assembly (e.g., Secondary Assembly 102).

FIG. 3A, FIG. 3B, FIG. 3C, and FIG. 3D illustrate a perspective view, bottom view, cross-sectional side view, and perspective view, respectively, of an example embodiment of the secondary assembly (e.g., secondary assembly 102). The secondary assembly 102 may include, resemble, and/or be formed as and/or in the shape of a cap, lip, cover, top, top portion, threaded bottle top, screw top or cap, or the like, for securing to and unsecuring from an example embodiment of the main assembly 101.

As further described below and in the present disclosure, the secondary assembly 102 may include one or more secondary securing portions 1021 for securing the main assembly 101 to the secondary assembly 102 (and/or for transitioning the storage assembly 100 between the secured state and the unsecured state). The secondary assembly 102 may also include one or more radiation assemblies 1022 for emitting or irradiating radiation into the main storage section 1012 of the main assembly 101. The secondary assembly 102 may also include one or more control assemblies 1023 for selectively controlling emission or irradiation of radiation by the one or more radiation assemblies 1022. In this regard, such controlling of emission or irradiation may include one or more elements, functions, actions, considerations, and/or checks to prevent unwanted, undesired, and/or unsafe emission or irradiation of radiation (e.g., preventing emissions or irradiation of radiation into an eye of a user and/or nearby persons/users, etc.). The secondary assembly 102 may also include one or more exterior surfaces 102a that forms at least a part of an exterior shape of the secondary assembly 102. The secondary assembly 102 may also include one or more interior surfaces 102b. As described in the present disclosure, the one or more exterior surfaces 102a of the secondary assembly 102 may include and/or form a part of a secondary securing portion 1021 when one or more interior surfaces 101b of the main assembly 101 include and/or form a part of the main securing portion 1013. Alternatively, the one or more interior surfaces 102b of the secondary assembly 102 may include and/or form a part of a secondary securing portion 1021 when one or more exterior surfaces 101a of the main assembly 101 include and/or form a part of the main securing portion 1013. The secondary assembly 102 may also include on or more other elements (not shown). For example, the secondary assembly 102 may include a graphical display (not shown), analog indicator, or the like, in communication with the control assembly 1023, radiation assembly 1022, and/or one or more other elements of the storage system 100, for displaying and/or providing an indication of, among other things, one or more of the following: a status of emission of radiation (e.g., by the radiation assembly 1022), signal/power/radiation level/amount of radiation (e.g., by the radiation assembly 1022), duration of emission of radiation (e.g., by the radiation assembly 1022), sanitization level/amount achieved by applying radiation (e.g., by the radiation assembly 1022), disinfection level/amount achieved by applying radiation (e.g., by the radiation assembly 1022), etc. Such communication between the control assembly 1023 (and/or radiation assembly 1022) and the graphical display/analog indicator (e.g., in example embodiments where the secondary assembly 102 includes the graphical display and/or the analog indicator), or the like, may be provided wirelessly and/or via an electrical connection/path. These elements of the secondary assembly 102 will now be further described below with reference to the accompanying figures, which form a part of the present disclosure.

The Secondary Securing Portion (e.g., Secondary Securing Portion 1021).

In an example embodiment, the secondary assembly 101 may include one or more secondary securing portions (e.g., secondary securing portion 1021). The one or more secondary securing portions 1021 may be configurable or configured to secure the main assembly 101 to the secondary assembly 102 (and unsecure the main assembly 101 from the secondary assembly 102). The one or more secondary securing portions 1021 may be configurable or configured to be transitioned between a secured state (which may correspond to a state in which the secondary securing portion 1021 is secured to a corresponding main securing portion 1013) and an unsecured state (which may correspond to a state in which the secondary securing portion 1021 is unsecured from a corresponding main securing portion 1013). Alternatively or in addition, the one or more secondary securing portions 1021 may be configurable or configured to transition the storage assembly 100 between the secured state and the unsecured state (as described in the present disclosure).

Figure 3A:
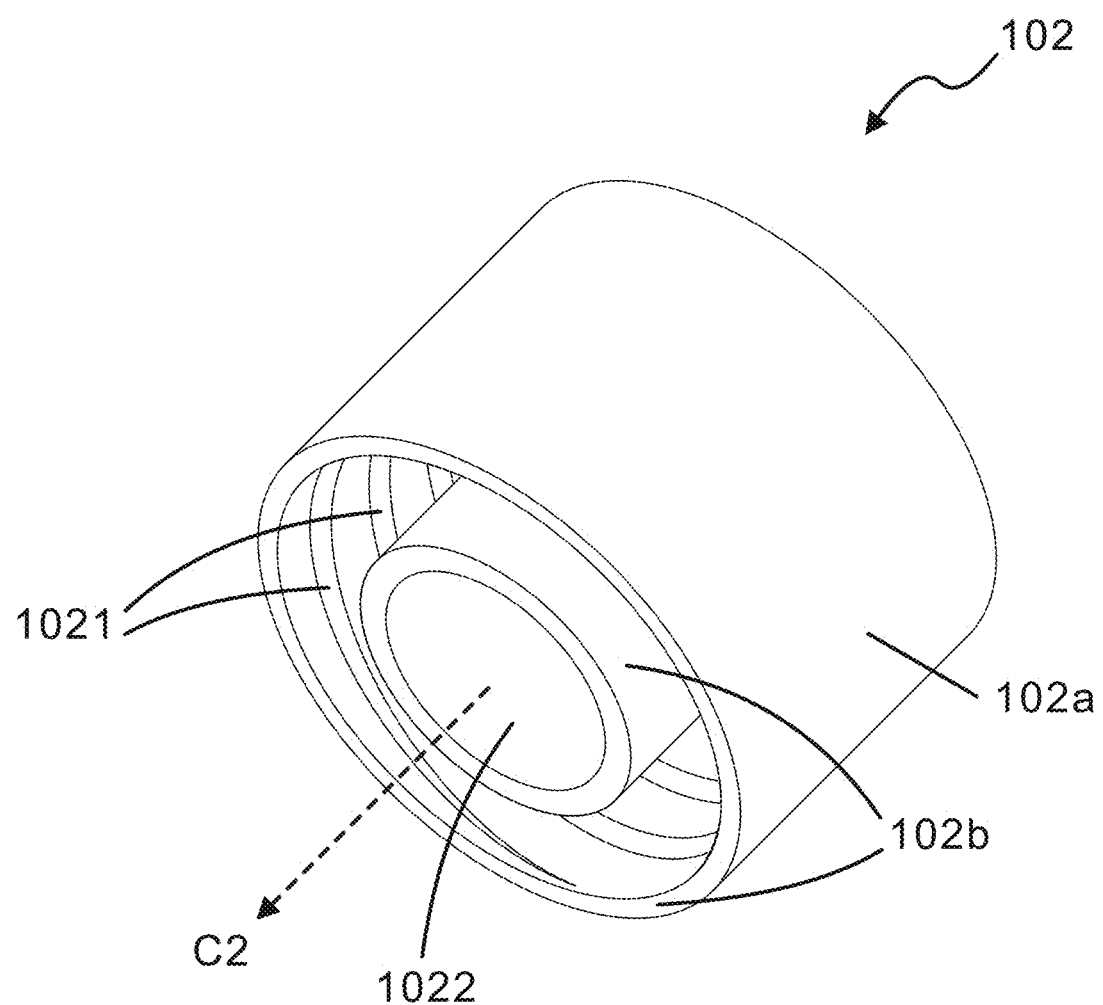
FIG. 3A illustrates a perspective view of an example embodiment of the secondary assembly.
Figure 3B:
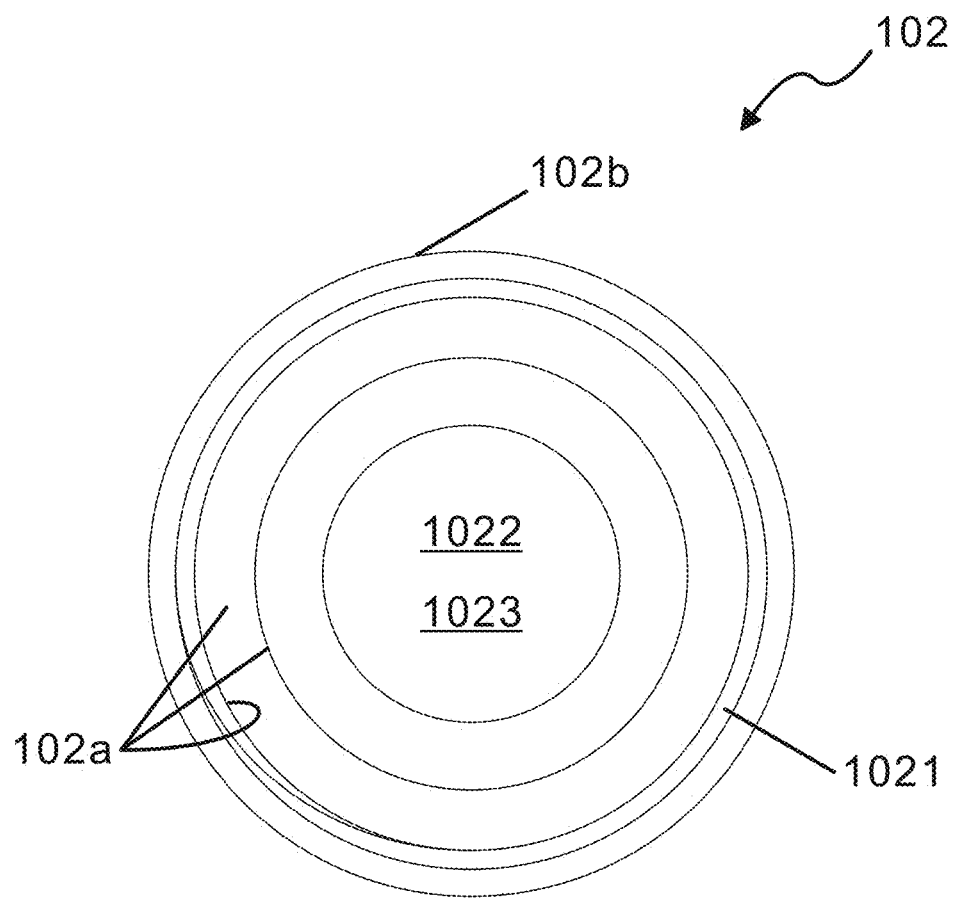
FIG. 3B illustrates a bottom view of an example embodiment of the secondary assembly.
Figure 3C:
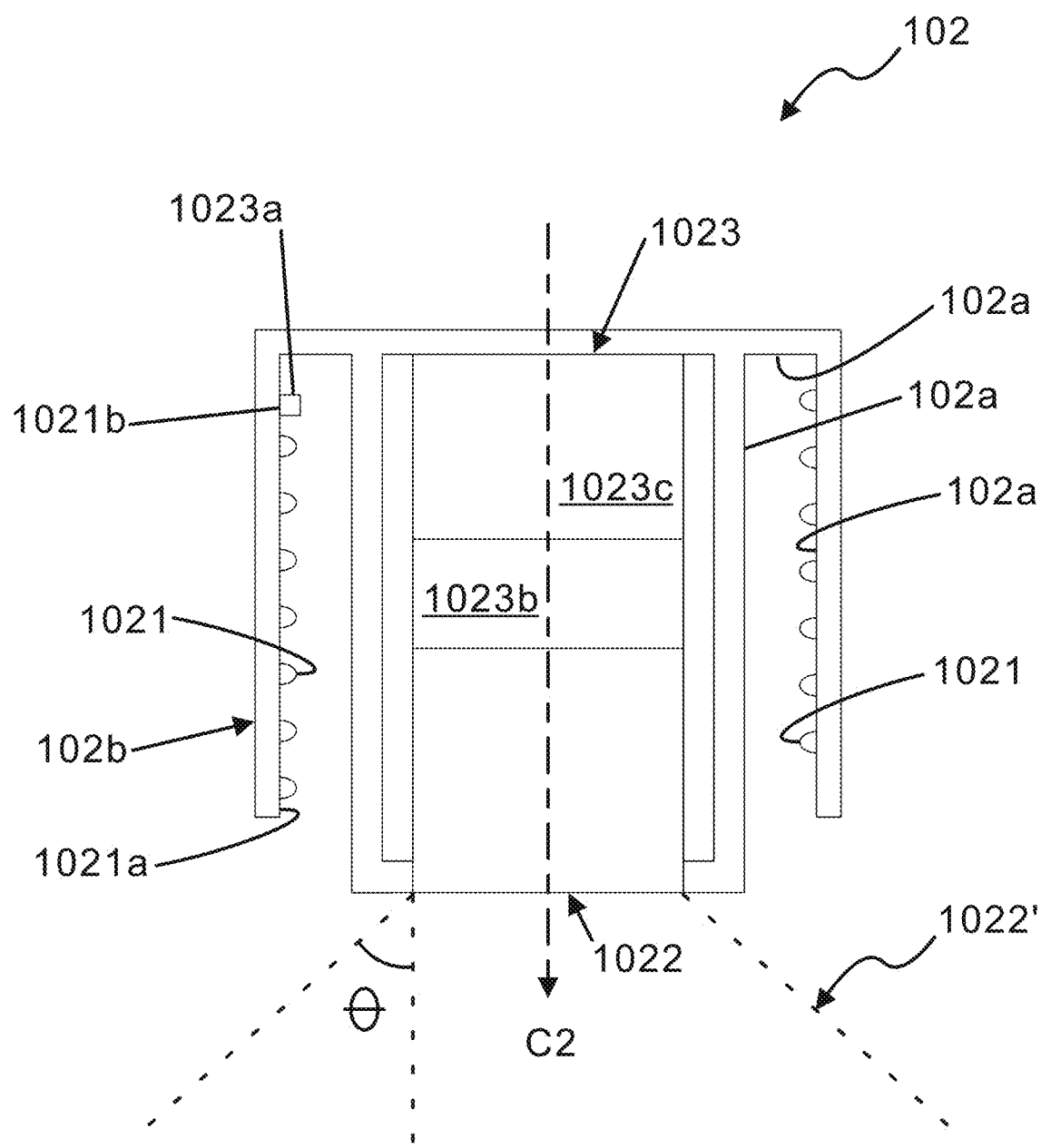
FIG. 3C illustrates a cross-sectional view of an example embodiment of the secondary assembly.
Figure 3D:
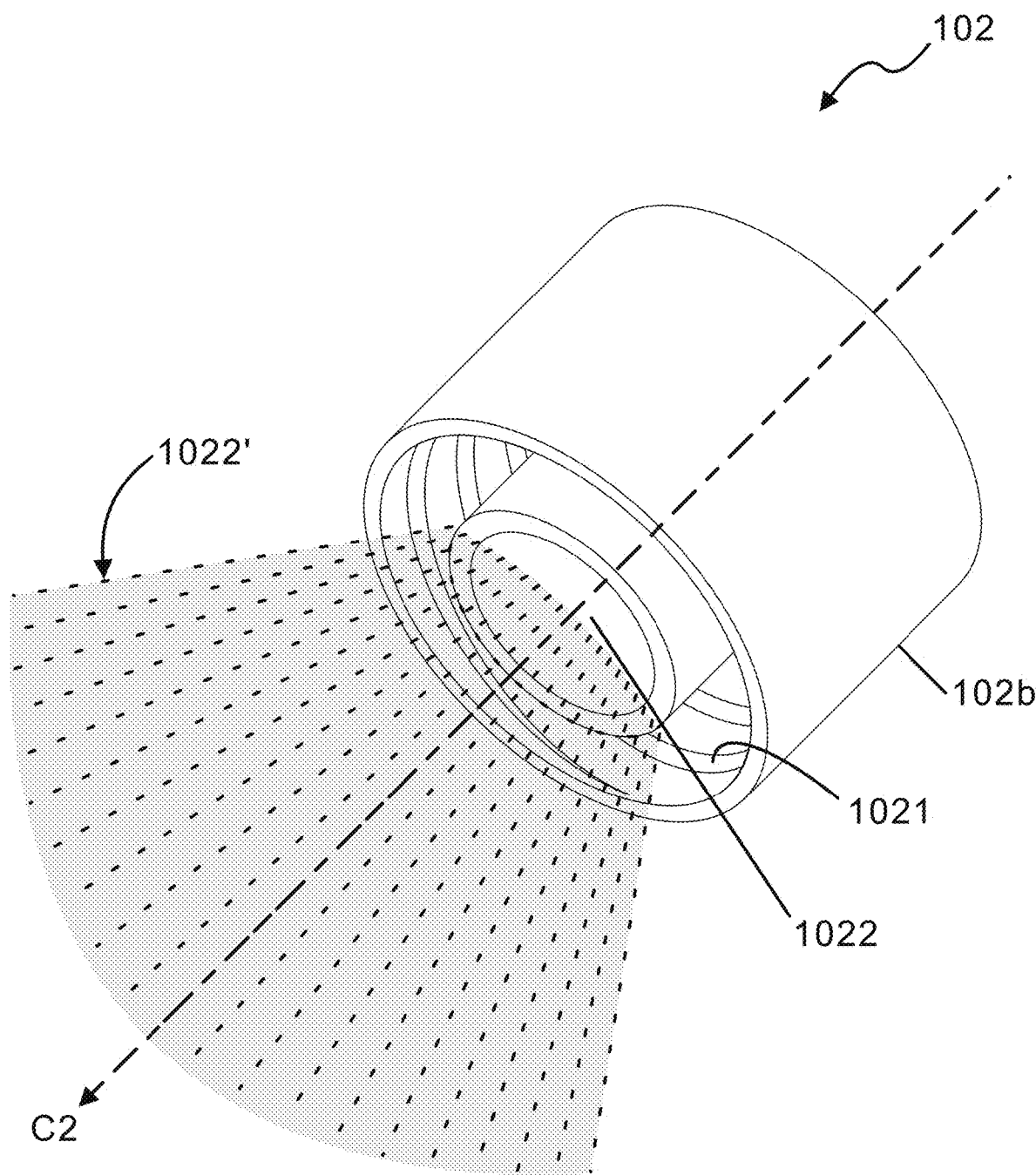
FIG. 3D illustrates a perspective view of an example embodiment of the secondary assembly and the radiation assembly emitting a conical-shaped radiation.

The secondary securing portion 1021 may be formed in one or of a plurality of configurations. For example, the secondary securing portion 1021 may be formed or provided as a threaded portion, such as those found in a threaded bottle top, threaded bottle top funnel, screw cap, or the like, on an interior surface 102b portion of the secondary assembly 102, in which case the main assembly 101 may also include a main securing portion 1013 having a complimentary or corresponding threaded portion on an exterior surface 102a of the main assembly 101 for receiving the threaded portion(s) of the secondary securing portion 1021. Alternatively, the secondary securing portion 1021 may be formed or provided as a threaded portion on an exterior surface 102a portion of the secondary assembly 102, in which case the main assembly 101 may also include a main securing portion 1013 having a complimentary or corresponding threaded portion on an interior surface 101b of the main assembly 101 for receiving the threaded portion(s) of the secondary securing portion 1021. FIGS. 3A, 3C and 3D illustrate example embodiments of the secondary securing portion 1021 having such threaded portions.

Alternatively or in addition, the secondary securing portion 1021 may be formed or provided as a push-button lock/unlock, latch lock/unlock, and/or any other securing/unsecuring configuration or mechanism without departing from the teachings of the present disclosure. In such embodiments, the main assembly 101 may also include a main securing portion 1013 formed or provided having a complimentary configuration or mechanism as the secondary securing portion 1021. It is to be understood in the present disclosure that the storage assembly 100 may also have a single securing portion (1013 and/or 1021) configurable or configured to secure the main assembly 101 to the secondary assembly 102 and configurable or configured to transition the storage assembly 100 between the secured state and the unsecured state (as described in the present disclosure) without departing from the teachings of the present disclosure.

The Radiation Assembly (e.g., Radiation Assembly 1022).

As illustrated in at least FIGS. 3A, 3C, and 3D, an example embodiment of the secondary assembly 102 may include one or more radiation assemblies (e.g., radiation assembly 1022). Each radiation assembly 1022 may be configurable or configured to emit or irradiate radiation 1022'. The radiation 1022' emittable or irradiatable by the radiation assembly 1022 may be any form, wavelength, frequency, magnitude/strength/level, configuration, etc., and for use in sanitizing, disinfecting, cleaning, de-contaminating, preserving, or the like, (referred to herein as "sanitization", "sanitizing", "disinfection", or "disinfecting") of the interior surface(s) 101b of the main storage section(s) 1012 and/or contents stored/housed in the main storage section(s) 1012. For example, the radiation 1022' emittable or irradiatable by the radiation assembly 1022 may include ultraviolet (UV) radiation 1022' including, but not limited to, UV-A, UV-B, and/or UV-C within any effective wavelength, frequency, or magnitude. Each radiation assembly 1022 may include or be formed having one or more radiation sources (e.g., UV LED bulbs, or the like). For example, the radiation assembly 1022 may include one radiation source having a central axis (such central axis C2 of the radiation assembly 1022 corresponding to a central axis C2 of radiation emittable or irradiatable by the one radiation source of the radiation assembly 1022). As another example, the radiation assembly 1022 may include four radiation sources having a central axis (such central axis of the radiation assembly 1022 corresponding to a central axis of radiation collectively emittable or irradiatable by the four radiation sources of the radiation assembly 1022). As another example, the radiation assembly 1022 may include a quantity of n (n being greater than 1) radiation sources having a central axis (such central axis of the radiation assembly 1022 corresponding to a central axis of radiation collectively emittable or irradiatable by the n radiation sources of the radiation assembly 1022). It is to be understood that, although the radiation assembly 1022 is described as being included with the secondary assembly 102, the radiation assembly 1022 (or one or more parts, elements, functions, or aspects of the radiation assembly 1022) may also be provided in (or performed by) the main assembly 101 without departing from the teachings of the present disclosure.

As illustrated in at least FIGS. 3C and 3D, the radiation assembly 1022 may be configurable or configured to emit or irradiate radiation 1022' within and/or covering a conical-shaped region (e.g., having a triangular-shaped cross-section), or the like. More specifically, the radiation 1022' emitted or irradiated by the radiation assembly 1022 (unless coming into contact with or being absorbed, blocked, and/or reflected by a radiation-absorbing, radiation-reflecting, and/or radiation-blocking object, such as an interior surface 101b of the main assembly 101 and/or contents stored or housed in the main storage section 1012) is conical (or substantially conical) in shape and/or having a shape resembling a filled cone. Such radiation 1022' covers the entire region within the conical-shaped region (unless blocked) ranging from a central axis C2 of the conical-shaped region (or central axis of the radiation assembly 1022) through to an exterior edge of the conical-shaped region (referred to herein as the "exterior of the conical-shaped region", "exterior of the cone", "edge of the conical-shaped region", "edge of the cone", or the like). In this regard, such conical-shaped region of the radiation 1022' may have a central axis C2 that is coaxial and/or parallel with a central axis of the radiation assembly 1022 (and/or central axis of the secondary assembly 102 and/or central axis of the main assembly 101 (when the secondary assembly 102 and main assembly 101 are in the secured state) and/or central axis of the main storage section 1012 (when the secondary assembly 102 and main assembly 101 are in the secured state)). In example embodiments, such conical-shaped region of the radiation 1022' may have (and/or be defined by) an angle of up to 80 degrees relative to the central axis of (or an axis parallel to the central axis of) the conical-shaped region (i.e., the exterior of the conical-shaped region may have an angle of up to 80 degrees relative to the central axis of the conical-shaped region). More preferably, such conical-shaped region of the radiation 1022' may have (and/or be defined by) an angle of up to 60 degrees relative to the central axis of the conical-shaped region (i.e., the exterior of the conical-shaped region may have an angle of up to 60 degrees relative to the central axis of the conical-shaped region), which may provide for a maximum sanitization area with minimum energy consumption (including achieving of better reflection of radiation from the contents stored in the main storage section 1012 and/or interior surface(s) 101*b* of the main storage section 1012). In some example embodiments, such conical-shaped region of the radiation 1022' may have (and/or be defined by) an angle of up to 40 degrees relative to the central axis of the conical-shaped region (i.e., the exterior of the conical-shaped region may have an angle of up to 40 degrees relative to the central axis of the conical-shaped region).

In an example embodiment, the radiation assembly 1022 may be formed symmetrically relative to a central axis C2 of the radiation assembly 1022 (e.g., as illustrated in at least FIG. 3D), and in this regard, the radiation 1022' (e.g., conical-shaped radiation) emittable or irradiatable by the radiation assembly 1022 may be symmetrical relative to the central axis C2 of the radiation assembly 1022. Alternatively or in addition, the radiation assembly 1022 may be formed symmetrically relative to a central axis C2 of the secondary assembly 102 (e.g., when the secondary assembly 102 has one radiation assembly 1022, the central axis C2 of the radiation assembly 1022 may be the same as, co-axial with, corresponding to, and/or parallel with the central axis C2 of the secondary assembly 102; when the secondary assembly 102 has more than one radiation assembly 1022, the central axis of each radiation assembly 1022 may be parallel with the central axis of the secondary assembly 102), and in this regard, the radiation 1022' (e.g., conical-shaped radiation) emittable or irradiatable by the radiation assembly 1022 may be symmetrical relative to the central axis C2 of the secondary assembly 102. Alternatively or in addition, the radiation assembly 1022 may be formed symmetrically relative to a central axis C1 of the main assembly 101 when the secondary assembly 102 and main assembly 101 are secured together in the secured state (e.g., when the secondary assembly 102 has one radiation assembly 1022, the central axis C2 of the radiation assembly 1022 may be the same as, co-axial with, corresponding to, and/or parallel with the central axis C1 of the main assembly 101; when the secondary assembly 102 has more than one radiation assembly 1022, the central axis of each radiation assembly 1022 may be parallel with the central axis C1 of the main assembly 101), and in this regard, the radiation 1022' (e.g., conical-shaped radiation) emittable or irradiatable by the radiation assembly 1022 may be symmetrical relative to the central axis C1 of the main assembly 101. Alternatively or in addition, the radiation assembly 1022 may be formed symmetrically relative to a central axis C1 of the main storage section 1012 when the secondary assembly 102 and main assembly 101 are secured together in the secured state (e.g., when the secondary assembly 102 has one radiation assembly 1022, the central axis C2 of the radiation assembly 1022 may be the same as, co-axial with, corresponding to, and/or parallel with the central axis C1 of the main storage section 1012; when the secondary assembly 102 has more than one radiation assembly 1022, the central axis of each radiation assembly 1022 may be parallel with the central axis of the main storage section 1012; when the secondary assembly 102 has more than one radiation assembly 1022 and the main assembly 101 has the same number of main storage sections 1012 as the number of radiation assemblies 1022, the central axis of each radiation assembly 1022 may be the same as, co-axial with, corresponding to, and/or parallel with the central axis of each main storage section 1012), and in this regard, the radiation 1022' (e.g., conical-shaped radiation) emittable or irradiatable by the radiation assembly 1022 may be symmetrical relative to the central axis of the main storage section 1012.

In example embodiments where the main assembly 101 includes one main opening 1011 and one main storage section 1012, the secondary assembly 102 may include one radiation assembly 1022. The radiation assembly 1022 may be configured to emit or irradiate radiation 1022' (e.g., conical-shaped radiation) in such a way as to reach, contact, cover, or the like, most or all of the interior surface 101*b* forming the main storage section 1012 (e.g., when the main storage section 1012 is not storing or housing any contents). Alternatively or in addition, the radiation assembly 1022 may be configured to collectively or cooperatively emit radiation 1022' (e.g., conical-shaped radiation) within or between about +/−80 degrees from a central axis C2 formed through the radiation assembly 1022 (i.e., the exterior of the conical-shaped radiation 1022' has an angle of up to 80 degrees relative to the central axis C2 formed by the radiation assembly 1022). More preferably, the radiation assembly 1022 is configured to collectively or cooperatively emit radiation 1022' (e.g., conical-shaped radiation) within or between about +/−about 60 degrees from the central axis C2 formed through the radiation assembly 1022 (i.e., the exterior of the conical-shaped radiation has an angle of up to 60 degrees relative to the central axis C2 formed by the radiation assembly 1022). In some embodiments, the radiation assembly 1022 may be configured to collectively or cooperatively emit radiation 1022' (e.g., conical-shaped radiation) within or between about +/−40 degrees from the central axis C2 formed through the radiation assembly 1022 (i.e., the exterior of the conical-shaped radiation 1022' has an angle of up to 40 degrees relative to the central axis formed by the radiation assembly 1022). Alternatively or in addition, the radiation assembly 1022 may be configured to collectively or cooperatively emit radiation 1022' (e.g., conical-shaped radiation) within or between about +/−80 degrees from a central axis C1 formed through the main assembly 101 when the secondary assembly 102 and the main assembly 101 are in a secured state (i.e., the exterior of the conical-shaped radiation 1022' has an angle of up to 80 degrees relative to the central axis C1 formed by the main assembly 102 when the secondary assembly 102 and the main assembly 101 are in a secured state). More preferably, the radiation assembly 1022 is configured to collectively or cooperatively emit radiation 1022' (e.g., conical-shaped radiation) within or between about +/−about 60 degrees from the central axis C1 formed through the main assembly 101 when the secondary assembly 102 and the main assembly 101 are in a secured state (i.e., the exterior of the conical-shaped radiation 1022' has an angle of up to 60 degrees relative to the central axis C1 formed by the main assembly 102 when the secondary assembly 102 and the main assembly 101 are in a secured state). In some embodiments, the radiation assembly 1022 may be configured to collectively or cooperatively emit radiation 1022' (e.g., conical-shaped radiation) within or between about +/−40 degrees from the central axis C1 formed through the main assembly 101 when the secondary assembly 102 and the main assembly 101 are in a secured state (i.e., the exterior of the conical-shaped radiation 1022' has an angle of up to 40 degrees relative to the central axis C1 formed by the main assembly 102 when the secondary assembly 102 and the main assembly 101 are in a secured state). Alternatively or in addition, the radiation assembly 1022 may be configured to collectively or cooperatively emit radiation 1022' (e.g., conical-shaped radiation) within or between about +/−80 degrees from a central axis C1 formed through the main storage section 1012 when the secondary assembly 102 and the main assembly 101 are in a secured state (i.e., the exterior of the conical-shaped radiation 1022' has an angle of up to 80 degrees relative to the central axis C1 formed by the main storage section 1012 when the secondary assembly 102 and the main assembly 101 are in a secured state). More preferably, the radiation assembly 1022 is configured to collectively or cooperatively emit radiation 1022' (e.g., conical-shaped radiation) within or between about +/−about 60 degrees from the central axis C1 formed through the main storage section 1012 when the secondary assembly 102 and the main assembly 101 are in a secured state (i.e., the exterior of the conical-shaped radiation 1022' has an angle of up to 60 degrees relative to the central axis C1 formed by the main storage section 1012 when the secondary assembly 102 and the main assembly 101 are in a secured state). In some embodiments, the radiation assembly 1022 may be configured to collectively or cooperatively emit radiation 1022' (e.g., conical-shaped radiation) within or between about +/−40 degrees from the central axis C1 formed through the main storage section 1012 when the secondary assembly 102 and the main assembly 101 are in a secured state (i.e., the exterior of the conical-shaped radiation 1022' has an angle of up to 40 degrees relative to the central axis C1 formed by the main storage section 1012 when the secondary assembly 102 and the main assembly 101 are in a secured state).

In example embodiments where the main assembly 101 includes two (or more) main openings 1011 and one main storage section 1012, the two (or more) main openings 1011 may be for use in receiving contents into the one main storage section 1012. In such embodiments, the secondary assembly 102 may include a first radiation assembly 1022 for a first main opening 1011 and a second radiation assembly 1022 for a second main opening 1011 (and one or more other radiation assemblies 1022 if there are more than two main openings 1011). The first and second radiation assemblies 1022 may be configured to collectively or cooperatively emit or irradiate radiation (e.g., conical-shaped radiation) in such a way as to reach, contact, cover, or the like, most or all of the interior surface 101b forming the one or more main storage sections 1012 (e.g., when the one or more main storage sections 1012 are not storing or housing any contents). Alternatively or in addition, each of the first and second radiation assemblies 1022 may be configured to emit or irradiate radiation 1022' (e.g., conical-shaped radiation) within or between about +/−80 degrees from a central axis formed through itself. More preferably, each of the first and second radiation assemblies 1022 are configured to emit radiation 1022' within or between about +/−about 60 degrees from the central axis formed through itself. In some embodiments, each of the first and second radiation assemblies 1022 may be configured to emit radiation 1022' (e.g., conical-shaped radiation) within or between about +/−40 degrees from the central axis formed through itself. Alternatively or in addition, each of the first and second radiation assemblies 1022 may be configured to emit or irradiate radiation 1022' (e.g., conical-shaped radiation) within or between about +/−80 degrees from a central axis C1 formed through the main assembly 101 when the secondary assembly 102 and the main assembly 101 are in a secured state. More preferably, each of the first and second radiation assemblies 1022 are configured to emit radiation 1022' (e.g., conical-shaped radiation) within or between about +/−about 60 degrees from the central axis C1 formed through the main assembly 101 when the secondary assembly 102 and the main assembly 101 are in a secured state. In some embodiments, each of the first and second radiation assemblies 1022 may be configured to emit radiation 1022' (e.g., conical-shaped radiation) within or between about +/−40 degrees from the central axis C1 formed through the main assembly 101 when the secondary assembly 102 and the main assembly 101 are in a secured state. Alternatively or in addition, the first and second radiation assemblies 1022 may be configured to collectively or cooperatively emit radiation 1022' (e.g., conical-shaped radiation) within or between about +/−80 degrees from a central axis C1 formed through the main storage section 1012 when the secondary assembly 102 and the main assembly 101 are in a secured state. More preferably, the first and second radiation assemblies 1022 are configured to collectively or cooperatively emit radiation 1022' (e.g., conical-shaped radiation) within or between about +/−about 60 degrees from the central axis C1 formed through the main storage section 1012 when the secondary assembly 102 and the main assembly 101 are in a secured state. In some embodiments, the first and second radiation assemblies 1022 may be configured to collectively or cooperatively emit radiation 1022' (e.g., conical-shaped radiation) within or between about +/−40 degrees from the central axis C1 formed through the main storage section 1012 when the secondary assembly 102 and the main assembly 101 are in a secured state. Alternatively, the secondary assembly 102 may include only one radiation assembly 1022 (e.g., a radiation assembly 1022 having a plurality radiation sources) configurable or configured to emit radiation 1022' (e.g., conical-shaped radiation) through or into the two (or more) main openings 1011. In example embodiments in which the main assembly 101 includes more than two main openings 1011, one main storage section 1012, and more than one radiation assembly 1022, each radiation assembly 1022 may be configurable or configured to emit radiation 1022' (e.g., conical-shaped radiation) through or into one or more main openings 1011 (and the number of main opening(s) 1011 receiving radiation 1022' from each radiation assembly 1022 may or may not be equal; e.g., a first main opening 1011 may receive radiation 1022' from a first radiation assembly 1022 and a second main opening 1011 may receive radiation 1022' from a second radiation assembly 1022 and a third radiation assembly 1022; etc.).

As another example, the main assembly 101 may include one main opening 1011 and two (or more) main storage sections 1012. In such an example, the one main opening 1011 may be for use in receiving contents into the two (or more) main storage sections 1012. In the same example, the secondary assembly 102 may include a first radiation assembly 1022 for one (or more) of the main storage sections 1012 and a second radiation assembly 1022 for the other one (or more) main storage section 1012. Alternatively, the secondary assembly 102 may include only one radiation assembly 1022 (e.g., having a plurality radiation sources) configurable or configured to emit radiation 1022' (e.g., conical-shaped radiation) into the two (or more) main storage sections 1012. In example embodiments in which the main assembly 101 includes one main opening 1011, more than two main storage section 1012, and more than one radiation assembly 1022, each radiation assembly 1022 may be configurable or configured to emit radiation 1022' (e.g., conical-shaped radiation) into one or more main storage sections 1012 (and the number of main storage sections 1012 receiving radiation 1022' from each radiation assembly 1022 may or may not be equal; e.g., a first main storage section 1012 may receive radiation 1022' from a first radiation assembly 1022 and a second main storage section 1012 may receive radiation 1022' from a second radiation assembly 1022 and a third radiation assembly 1022; etc.).

The Control Assembly (e.g., Control Assembly 1023)

In an example embodiment, the secondary assembly 102 may include one or more control assemblies (e.g., control assembly 1023). Each control assembly 1023 may be configurable or configured to selectively control the one or more radiation assemblies 1022, including selectively controlling the emission or irradiation of radiation (e.g., conical-shaped radiation) by the one or more radiation assemblies 1022. Such controlling of emission or irradiation of radiation by the one or more radiation assemblies 1022 may include preventing of unwanted, undesired, and/or unsafe emission or irradiation of radiation (e.g., preventing emissions or irradiation of radiation into an eye of a user and/or nearby persons/users, etc.).

As further described below and in the present disclosure, the control assembly 1023 may include one or more first safety assemblies 1023a for determining whether the storage system 100 is in the secured state or the unsecured state (e.g., whether the main securing portion 1013 and secondary securing portion 1021 are secured together or not; whether the main assembly 101 and the secondary assembly 102 are secured together or not; and/or whether the main assembly 101 and the secondary assembly 102 are in the secured state or unsecured state). The control assembly 1023 may also include one or more second safety assemblies 1023b for determining whether the secondary assembly 102 is in a safe orientation state or an unsafe orientation state. The control assembly 1023 may also include one or more control processors 1023c for selectively controlling the radiation assembly 1022 to emit or irradiate radiation based on at least a cooperation with the first safety assembly 1023a and/or the second safety assembly 1023b. It is to be understood that, although the control assembly 1023 is described as being included with the secondary assembly 102, the control assembly 1023 (or one or more parts, elements, functions, or aspects of the control assembly 1023) may also be provided in (or performed by) the main assembly 101 without departing from the teachings of the present disclosure. These elements of the secondary assembly 102 will now be further described below with reference to the accompanying figures, which form a part of the present disclosure.

i. The First Safety Assembly (e.g., First Safety Assembly 1023a).

In an example embodiment, the control assembly 1023 may include a first safety assembly (e.g., first safety assembly 1023a). The first safety assembly 1023a is configurable or configured to determine whether the storage system 100 is in the secured state or the unsecured state.

As described in the present disclosure, the secured state may be a state in which the main assembly 101 and the secondary assembly 102 are secured together via the one or more securing portions (e.g., securing portion(s) formed on the main assembly 101; securing portion(s) formed on the secondary assembly 102; securing portion(s) formed on both main assembly 101 and secondary assembly 102; or securing portion(s) not formed on either the main assembly 101 or secondary assembly 102, such as securing portion(s) that are and/or become a separate element from the main assembly 101 and the secondary assembly 102 when such securing portion(s) are not used to secure the main assembly 101 and the secondary assembly 102 together). Alternatively or in addition, the secured state may be a state in which the main assembly 101 and the secondary assembly 102 are secured together in a hermetically sealed manner (and/or water-proof manner and/or air-tight manner) via the one or more securing portions. In some embodiments, the secured state may be a state in which the main assembly 101 and the secondary assembly 102 are secured together via the one or more securing portions, but not necessarily secured together in a hermetically sealed manner (or water-proof manner or air-tight manner). Put differently, the secured state in such an example may be either of the following states: a state in which the main assembly 101 and the secondary assembly 102 are either secured together in a hermetically sealed manner via the securing assembly; or a state in which the main assembly 101 and the secondary assembly 102 are either secured together in a non-hermetically sealed manner via the securing assembly). In terms of the unsecured state, the unsecured state may be a state in which the main assembly 101 and the secondary assembly 102 are not secured together via the one or more securing portions. For example, in example embodiments where the secured state is a state in which the main assembly 101 and the secondary assembly 102 are secured together in a hermetically sealed manner (and/or water-proof manner and/or air-tight manner) via the one or more securing portions, the unsecured state may be any of the following states: a state in which the main assembly 101 and the secondary assembly 102 are not secured together at all (e.g., the state or configuration illustrated in FIG. 1B); or a state in which the main assembly 101 and the secondary assembly 102 are secured together, but not in a hermetically sealed manner (or water-proof manner or air-tight manner). Alternatively, in example embodiments where the secured state is a state in which the main assembly 101 and the secondary assembly 102 are secured together via the one or more securing portions, but not necessarily secured together in a hermetically sealed manner (or water-proof manner or air-tight manner) (i.e., may or may not be hermetically sealed), the unsecured state for such storage systems 100 will be a state in which the main assembly 101 and the secondary assembly 102 are not secured together at all (e.g., the state or configuration illustrated in FIG. 1B).

In order to determine whether the storage assembly 101 is in the secured state or the unsecured state, the first safety assembly 1023a may include one or more elements configurable or configured to communicate with the control processor 1023c.

For example, the first safety assembly 1023a may include a contact sensor, or the like, in cooperation with the main securing portion 1013 and/or secondary securing portion 1021 to determine whether or not the main securing portion 1013 and the secondary securing portion 1021 are secured together (and/or whether they are in a secured state or an unsecured state). As a more specific example, when the main securing portion 1013 and the secondary securing portion 1021 are provided in the form of a threaded portion (e.g., threaded bottle top, threaded bottle top funnel, screw cap, or the like), or the like, the first safety assembly 1023a may include a contact sensor, or the like, at a distal end 1013b, 1021b or end region 1013b, 1021b (and/or most distal or most furthest point) of the threaded portion of the main securing portion 1013 and/or the threaded portion of the secondary securing portion 1021. In such an example, when the main securing portion 1013 and secondary securing portion 1021 become secured together (i.e., a distal end 1013*b* or end point/region 1013 of the threaded portion of the main securing portion 1013 comes into contact with a proximal end 1021*a* or starting point/region 1021*a* of the threaded portion of the secondary securing portion 1021; and a proximal end 1013*a* or starting point/region 1013*a* of the threaded portion of the main securing portion 1013 comes into contact with a distal end 101*b* or end point/region 1021*b* of the threaded portion of the secondary securing portion 1021), one or more of the following apply: when a contact sensor is provided at the distal end 1013*b* or end point/region 1013*b* of the threaded portion of the main securing portion 1013, the proximal end 1021*a* or starting point/region 1021*a* of the threaded portion of the secondary securing portion 1021 will come into contact with the contact sensor, and the first safety assembly 1023 will send a communication signal to the control processor 1023*c* (in which case, the control processor 1023*c* identifies that the storage assembly 100 is in the secured state); when a contact sensor is provided at the distal end 101*b* or end point/region 1021*b* of the threaded portion of the secondary securing portion 1021, the proximal end 1013*a* or starting point/region 1013*a* of the threaded portion of the main securing portion 1013 will come into contact with the contact sensor, and the first safety assembly 1023 will send a communication signal to the control processor 1023*c* (which identifies that the storage assembly 100 is in the secured state); or when a first contact sensor is provided at the distal end 1013*b* or end point/region 1013*b* of the threaded portion of the main securing portion 1013 and a second contact sensor is provided at the distal end 1021*b* or end point/region 1021*b* of the threaded portion of the secondary securing portion 1021, the proximal end 1021*a* or starting point/region 1021*a* of the threaded portion of the secondary securing portion 1021 will come into contact with the first contact sensor and the proximal end 1013*a* or starting point/region 1013*a* of the threaded portion of the main securing portion 1013 will come into contact with the second contact sensor, and the first safety assembly 1023 will send a communication signal to the control processor 1023*c* based on the receiving of both communication signals from the first and second contact sensors (in which case, the control processor 1023*c* identifies that the storage assembly 100 is in the secured state).

As another more specific example, when the main securing portion 1013 and the secondary securing portion 1021 are provided with cooperating elements that form of a push-button locking mechanism (and/or push-type locking mechanism, pull-type locking mechanism, twist-type locking mechanism, snap-lock-type locking mechanism, or the like), the first safety assembly 1023*a* may include a contact sensor, or the like, in and/or on the main securing portion 1013 and/or the secondary securing portion 1021. In such an example, when the main securing portion 1013 and secondary securing portion 1021 become secured together, the element(s) of the push-button locking mechanism of the main securing portion 1013 and/or the element(s) of the push-button locking mechanism of the secondary securing portion 1013 will come into contact with the contact sensor, and the first safety assembly 1023 will send a communication signal to the control processor 1023*c* (in which case, the control processor 1023*c* identifies that the storage assembly 100 is in the secured state).

In yet another more specific example, an interior surface 102*b* of the secondary assembly 102 and/or an interior surface 101*b* of the main assembly 101 may include a light sensor, or the like. In such an example, when the main securing portion 1013 and secondary securing portion 1021 become secured together (in any one or more ways, including those described in the present disclosure), the one or more light sensors will detect an absence of light, and the first safety assembly 1023 will send a communication signal to the control processor 1023*c* (in which case, the control processor 1023*c* identifies that the storage assembly 100 is in the secured state).

ii. The Second Safety Assembly (e.g., Secondary Safety Assembly 1023*b*).

In an example embodiment, the control assembly 1023 may include a second safety assembly (e.g., second safety assembly 1023*b*). The second safety assembly 1023*b* is configurable or configured to determine whether the storage system 100 is in a safe orientation state or an unsafe orientation state.

In terms of the safe orientation state of the storage assembly 100, the safe orientation state may be a state in which the main assembly 101 and/or the secondary assembly 102 is/are oriented in one or more specific safe orientations or ranges of safe orientations. For example, a safe orientation state may be a state in which an orientation of the main assembly 101 is exactly upright or within a predetermined threshold of being exactly upright. Put differently, the safe orientation state may be a state in which the orientation of the main assembly 101 (and/or central axis C1 of the main assembly 101; and/or central axis C1 of the main storage section 1012) is parallel or within a predetermined threshold of being parallel to a zero-slope vertical axis. As used in the present disclosure, a "zero-slope vertical axis" may refer to a vertical axis, zero-slope axis, y-axis in a Cartesian coordinate system, axis pointing in a directly downward direction, axis pointing in a direction in which an object would fall towards the ground without any external forces or influences other than gravity, etc. Put differently, the safe orientation state may be a state in which an absolute value of an angular difference between the central axis C1 of the main assembly 101 (and/or central axis C1 of the main storage section 1012) and the zero-slope vertical axis is less than or equal to a predetermined threshold. In example embodiments, the predetermined threshold may be between about 0 to 45 degrees, and more preferably, less than or equal to about 30 degrees, and even more preferably, less than or equal to about 15 degrees. As another example, the safe orientation state may be a state in which the orientation of the secondary assembly 102 is exactly upright or within a predetermined threshold of being exactly upright. Put differently, the safe orientation state may be a state in which the orientation of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) is parallel or within a predetermined threshold of being parallel to the zero-slope vertical axis. Put differently, the safe orientation state may be a state in which an absolute value of an angular difference between the central axis C2 of the secondary assembly 102 (and/or central axis of the secondary assembly 102; and/or central axis C2 of the radiation assembly 1022; and/or central axis of the conical-shaped radiation emitted or irradiated by the radiation assembly 1022) and the zero-slope vertical axis is less than or equal to the predetermined threshold. As another example, the safe orientation state may be a state in which the orientation of both the main assembly 101 and the secondary assembly 102 are exactly upright or within a predetermined threshold of being exactly upright. Alternatively or in addition, the safe orientation state may be a state in which the orientation of both the main assembly 101 (and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are the same or within a predetermined threshold of being the same. Alternatively or in addition, the safe orientation state may be a state in which the orientation of both the main assembly 101 (and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are parallel or within the predetermined threshold of being parallel to the zero-slope vertical axis. Alternatively or in addition, the safe orientation state may be a state in which: an absolute value of an angular difference between the central axis of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) and the zero-slope vertical axis is less than or equal to the predetermined threshold; and an absolute value of an angular difference between the central axis of the main assembly 101 (and/or central axis C1 of the main storage section 1012) and the zero-slope vertical axis is less than or equal to the predetermined threshold.

The unsafe orientation state of the storage assembly 100, on the other hand, may be a state in which the main assembly 101 and/or the secondary assembly 102 is/are oriented in one or more specific unsafe orientations or ranges of unsafe orientations. For example, when a safe orientation state is a state in which an orientation of the main assembly 101 is exactly upright (or within a predetermined threshold of being exactly upright), an unsafe orientation is a state in which the orientation of the main assembly 101 is not exactly upright (or not within a predetermined threshold of being exactly upright). When the safe orientation state is a state in which the orientation of the main assembly 101 (and/or central axis C1 of the main assembly 101; and/or central axis C1 of the main storage section 1012) is parallel (or within a predetermined threshold of being parallel) to the zero-slope vertical axis, the unsafe orientation state is a state in which the orientation of the main assembly 101 (and/or central axis C1 of the main assembly 101; and/or central axis C1 of the main storage section 1012) is not parallel (or not within a predetermined threshold of being parallel) to the zero-slope vertical axis. When the safe orientation state is a state in which an absolute value of an angular difference between the central axis C1 of the main assembly 101 (and/or central axis C1 of the main storage section 1012) and the zero-slope vertical axis is less than or equal to a predetermined threshold, the unsafe orientation state is a state in which an absolute value of an angular difference between the central axis C1 of the main assembly 101 (and/or central axis C1 of the main storage section 1012) and the zero-slope vertical axis is greater than the predetermined threshold. When the safe orientation state is a state in which the orientation of the secondary assembly 102 is exactly upright (or within a predetermined threshold of being exactly upright), the unsafe orientation state is a state in which the orientation of the secondary assembly 102 is not exactly upright (or not within a predetermined threshold of being exactly upright). When the safe orientation state may be a state in which the orientation of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) is parallel (or within a predetermined threshold of being parallel) to the zero-slope vertical axis, the unsafe orientation state is a state in which the orientation of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) is not parallel (or within a predetermined threshold of being parallel) to the zero-slope vertical axis. When the safe orientation state is a state in which an absolute value of an angular difference between the central axis of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) and the zero-slope vertical axis is less than or equal to the predetermined threshold, the unsafe orientation state is a state in which an absolute value of an angular difference between the central axis C2 of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) and the zero-slope vertical axis is greater than the predetermined threshold. When the safe orientation state is a state in which the orientation of both the main assembly 101 and the secondary assembly 102 are exactly upright (or within a predetermined threshold of being exactly upright), the unsafe orientation state is a state in which the orientation of both the main assembly 101 and the secondary assembly 102 are not exactly upright (or not within a predetermined threshold of being exactly upright). When the safe orientation state is a state in which the orientation of both the main assembly 101 (and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are the same (or within a predetermined threshold of being the same), the unsafe orientation state is a state in which the orientation of both the main assembly 101 (and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are not the same (or not within a predetermined threshold of being the same). When the safe orientation state is a state in which the orientation of both the main assembly 101 (and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are parallel (or within the predetermined threshold of being parallel to the zero-slope vertical axis), the unsafe orientation state is a state in which the orientation of both the main assembly 101

(and/or central axis C1 of the main assembly 101; or central axis C1 of the main storage section 1012) and the secondary assembly 102 (and/or central axis C2 of the secondary assembly 102; and/or central axis C2 of the radiation assembly 1022; and/or central axis of the conical-shaped radiation emitted or irradiated by the radiation assembly 1022) are not parallel (or not within the predetermined threshold of being parallel to the zero-slope vertical axis). When the safe orientation state is a state in which: an absolute value of an angular difference between the central axis C2 of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) and the zero-slope vertical axis is less than or equal to the predetermined threshold; and an absolute value of an angular difference between the central axis C1 of the main assembly 101 (and/or central axis C1 of the main storage section 1012) and the zero-slope vertical axis is less than or equal to the predetermined threshold, the unsafe orientation state is a state in which: an absolute value of an angular difference between the central axis C2 of the secondary assembly 102 (and/or central axis C2 of the secondary assembly 102; and/or central axis C2 of the radiation assembly 1022; and/or central axis of the conical-shaped radiation emitted or irradiated by the radiation assembly 1022) and the zero-slope vertical axis is greater than the predetermined threshold; and an absolute value of an angular difference between the central axis C1 of the main assembly 101 (and/or central axis C1 of the main storage section 1012) and the zero-slope vertical axis is greater than the predetermined threshold.

In order to determine whether the storage assembly 101 is in the safe orientation state or the unsafe orientation state, the second safety assembly 1023a may include one or more elements configurable or configured to communicate with the control processor 1023c.

For example, the second safety assembly 1023b may include a gravity-related sensor, or the like, to determine an orientation of the main assembly 101, one or more elements of the main assembly 101, the secondary assembly 102, and/or one or more elements of the secondary assembly 102. Alternatively or in addition, the gravity-related sensor may be configurable or configured to determine an orientation of the main assembly 101, one or more elements of the main assembly 101, the secondary assembly 102, and/or one or more elements of the secondary assembly 102 relative to the zero-slope vertical axis. Alternatively or in addition, the gravity-related sensor may be configurable or configured to determine an orientation of the main assembly 101 and/or one or more elements of the main assembly 101 relative to the secondary assembly 102 and/or one or more elements of the secondary assembly 102. Example embodiments of the gravity-related sensor may include, but are not limited to, gyroscopes, accelerometers, motion sensors, rotation vector sensors, geomagnetic field sensors, orientation sensors, or the like.

As another example, the second safety assembly 1023b may include a pressure sensor, or the like, provided in an interior surface 102b of the secondary assembly 102 to determine whether there is pressure (and/or an amount of pressure) exerted by contents (e.g., liquid, such as water) stored in the main storage section 1012. As a more specific example, in situations where the secondary assembly 102 is in an upside-down orientation (e.g., the radiation assembly 1022 is pointing directly upwards, or within a predetermined threshold of a directly upwards direction) and the pressure sensor of the second safety assembly 1023b detects or measures a sufficient pressure (which represents liquid contents resting on or pushing downward onto the pressure sensor), then second safety assembly 1023b may be configured to send a communication signal to the control processor 1023c, which may identify the storage system 100 to be in a safe orientation state. Alternatively or in addition, the second safety assembly 1023b may include a pressure sensor, or the like, provided in an interior surface 102b (e.g., bottom wall) of the main storage section 1012 to determine whether there is pressure (and/or an amount of pressure) exerted by contents (e.g., liquid, such as water) stored in the main storage section 1012. As a more specific example, in situations where the main assembly 101 is in an upright orientation (e.g., the radiation assembly 1022 is pointing directly downwards, or within a predetermined threshold of a directly upwards direction, when the main assembly 101 is secured to the secondary assembly 102) and the pressure sensor of the second safety assembly 1023b (located at the bottom wall of the main storage section 1012) detects or measures a sufficient pressure (which represents liquid contents resting on or pushing downward onto the pressure sensor), then second safety assembly 1023b may be configured to send a communication signal to the control processor 1023c, which may identify the storage system 100 to be in a safe orientation state.

iii. The Control Processor (e.g., Control Process 1023c).

As illustrated in at least FIG. 6, the control assembly 1023 may include a control processor (e.g., control processor 1023c). The control processor 1023c may be configurable or configured to selectively control the radiation assembly 1022 turn on or off, that is, to emit/irradiate radiation or to not emit/irradiate radiation. The control processor 1023c performs the selective controlling of the radiation assembly 1022 based on at least a cooperation with the first safety assembly 1023a and/or the second safety assembly 1023b. In this regard, the control processor 1023c is configurable or configured to communicate with one or more elements of the first safety assembly 1023a and/or one or more elements of the second safety assembly 1023b.

Example 1: The Control Processor 1023c Selectively Controlling the Radiation Assembly 1022 to Emit/Irradiate Radiation In an example embodiment of the storage system 100, the control processor 1023c is configured to selectively control the radiation assembly 1022 to emit/irradiate radiation when the control processor 1023c determines, based on communications received from the first safety assembly 1023a and the second safety assembly 1023b, that the storage system 100 is in the secured state and the safe orientation state. The secured state may be determined based on any one or more embodiments described in the present disclosure, including, but not limited to, a light sensor provided on an interior surface 101b and/or interior surface 102b; a contact sensor provided in or on the main securing portion 1013, the secondary securing portion 1021, and/or one or more portions that come into contact with one another when the main assembly 101 and the secondary assembly 102 are secured together (e.g., a bottom portion of the secondary assembly 102 and a top portion of the main assembly 101); etc. The safe orientation state may be determined based on any one or more embodiments described in the present disclosure, including, but not limited to, a gravity-related sensor to determine orientation information of or pertaining to the main assembly 101, one or more elements of the main assembly 101, the secondary assembly 102, and/or one or more elements of the secondary assembly 102.

Example 2: The Control Processor 1023c Selectively Controlling the Radiation Assembly 1022 to not Emit/Irradiate Radiation In an example embodiment of the storage system 100, the control processor 1023c is configured to selectively control the radiation assembly 1022 to not emit/irradiate radiation when the control processor 1023c determines, based on communications received (and/or not received) from the first safety assembly 1023a and/or the second safety assembly 1023b, that the storage system 100 is in the secured state and the unsafe orientation state. The secured state may be determined based on any one or more embodiments described in the present disclosure. The unsafe orientation state may be determined based on any one or more embodiments described in the present disclosure.

Example 3: The Control Processor 1023c Selectively Controlling the Radiation Assembly 1022 to not Emit/Irradiate Radiation In an example embodiment of the storage system 100, the control processor 1023c is configured to selectively control the radiation assembly 1022 to not emit/irradiate radiation when the control processor 1023c determines, based on communications received (and/or not received) from the first safety assembly 1023a and/or the second safety assembly 1023b, that the storage system 100 is in the unsecured state and the safe orientation state. The unsecured state may be determined based on any one or more embodiments described in the present disclosure. The safe orientation state may be determined based on any one or more embodiments described in the present disclosure.

Example 4: The Control Processor 1023c Selectively Controlling the Radiation Assembly 1022 to not Emit/Irradiate Radiation In an example embodiment of the storage system 100, the control processor 1023c is configured to selectively control the radiation assembly 1022 to not emit/irradiate radiation when the control processor 1023c determines, based on communications received (and/or not received) from the first safety assembly 1023a and/or the second safety assembly 1023b, that the storage system 100 is in the unsecured state and the unsafe orientation state. The unsecured state may be determined based on any one or more embodiments described in the present disclosure. The unsafe orientation state may be determined based on any one or more embodiments described in the present disclosure.

While various embodiments in accordance with the disclosed principles have been described above, it should be understood that they have been presented by way of example only, and are not limiting. Thus, the breadth and scope of the example embodiments described in the present disclosure should not be limited by any of the above-described exemplary embodiments, but should be defined only in accordance with the claims and their equivalents issuing from this disclosure. Furthermore, the above advantages and features are provided in described embodiments, but shall not limit the application of such issued claims to processes and structures accomplishing any or all of the above advantages.

For example, as referred to herein, a controller, processor, control processor (e.g., control processor 1023c), and/or device may be any computing device or communication device, and may include a virtual machine, computer, node, instance, host, or machine in a networked computing environment. Also as referred to herein, a network or cloud may be a collection of machines connected by communication channels that facilitate communications between machines and allow for machines to share resources. Network may also refer to a communication medium between processes on the same machine. Also as referred to herein, a network element, node, or server may be a machine deployed to execute a program operating as a socket listener and may include software instances.

Memory (or storage or database) may comprise any collection and arrangement of volatile and/or non-volatile components suitable for storing data. For example, memory may comprise random access memory (RAM) devices, read-only memory (ROM) devices, magnetic storage devices, optical storage devices, and/or any other suitable data storage devices. In particular embodiments, memory may represent, in part, computer-readable storage media on which computer instructions and/or logic are encoded. Memory may represent any number of memory components within, local to, and/or accessible by a processor.

Various terms used herein have special meanings within the present technical field. Whether a particular term should be construed as such a "term of art" depends on the context in which that term is used. Terms are to be construed in light of the context in which they are used in the present disclosure and as one of ordinary skill in the art would understand those terms in the disclosed context. Definitions provided herein are not exclusive of other meanings that might be imparted to those terms based on the disclosed context.

Words of comparison, measurement, and timing such as "at the time", "equivalent", "during", "complete", and the like should be understood to mean "substantially at the time", "substantially equivalent", "substantially during", "substantially complete", etc., where "substantially" means that such comparisons, measurements, and timings are practicable to accomplish the implicitly or expressly stated desired result.

Additionally, the section headings and topic headings herein are provided for consistency with the suggestions under various patent regulations and practice, or otherwise to provide organizational cues. These headings shall not limit or characterize the embodiments set out in any claims that may issue from this disclosure. Specifically, a description of a technology in the "Background" is not to be construed as an admission that technology is prior art to any embodiments in this disclosure. Furthermore, any reference in this disclosure to "invention" in the singular should not be used to argue that there is only a single point of novelty in this disclosure. Multiple inventions may be set forth according to the limitations of the claims issuing from this disclosure, and such claims accordingly define the invention(s), and their equivalents, that are protected thereby. In all instances, the scope of such claims shall be considered on their own merits in light of this disclosure, but should not be constrained by the headings herein.

What is claimed is:

1. A liquid storage system, the liquid storage system comprising:
   a main assembly, the main assembly having:
      a main opening; and
      a main storage section, the main storage section configured to receive a liquid via the main opening; and a secondary assembly, the secondary assembly including:
  a securing portion, the securing portion transitionable between a secured state and an unsecured state, the secured state being a state in which the main assembly and the secondary assembly are secured together via the securing portion, the unsecured state being a state in which the main assembly and the secondary assembly are not secured together;
  a radiation assembly, the radiation assembly configured to emit UV radiation, the radiation assembly formed symmetrically relative to a first central axis; and
  a control assembly, the control assembly including:
    a first safety assembly, the first safety assembly configured to determine whether the liquid storage system is in the secured state or the unsecured state;
    a second safety assembly, the second safety assembly configured to determine whether the secondary assembly is in a safe orientation state or an unsafe orientation state; and
    a control processor, the control processor configured to control the radiation assembly to emit the UV radiation when:
      the first safety assembly determines that the liquid storage system is in the secured state; and
      the second safety assembly determines that the secondary assembly is in the safe orientation state.

2. The liquid storage system of claim 1, wherein:
the radiation assembly is configured to emit UV radiation within a conical-shaped region, the conical-shaped region being coaxial with the radiation assembly, the conical-shaped region having an angle of not more than 80 degrees and not less than 40 degrees relative to the first central axis.

3. The liquid storage system of claim 2, wherein:
the conical-shaped region has an angle of not more than 70 degrees and not less than 50 degrees relative to the first central axis.

4. The liquid storage system of claim 2, wherein:
the conical-shaped region has an angle of 60 degrees relative to the first central axis.

5. The liquid storage system of claim 1, wherein:
the radiation assembly includes one or more UV radiation sources;
each of the one or more UV radiation sources are configured to emit UV radiation within a conical-shaped region, each conical-shaped region having a central axis parallel to the first central axis; and
each conical-shaped region has an angle of not more than 80 degrees and not less than 40 degrees relative to the first central axis.

6. The liquid storage system of claim 5, wherein:
each conical-shaped region has an angle of not more than 70 degrees and not less than 50 degrees relative to the first central axis.

7. The liquid storage system of claim 5, wherein:
each conical-shaped region has an angle of 60 degrees relative to the first central axis.

8. The liquid storage system of claim 1, wherein:
the first safety assembly includes a light sensor, the light sensor configured to detect a presence of visible light;
the first safety assembly determines that the liquid storage system is in the secured state when the light sensor does not detect the presence of visible light; and
the first safety assembly determines that the liquid storage system is in the unsecured state when the light sensor detects the presence of visible light.

9. The liquid storage system of claim 1, wherein:
the first safety assembly includes a contact sensor;
the contact sensor is configured to detect whether or not the main assembly and the secondary assembly are secured together via the securing portion;
the first safety assembly determines that the liquid storage system is in the secured state when the contact sensor detects that the main assembly and the secondary assembly are secured together via the securing portion; and
the first safety assembly determines that the liquid storage system is in the unsecured state when the contact sensor detects that the main assembly and the secondary assembly are not secured together via the securing portion.

10. The liquid storage system of claim 1, wherein:
the safe orientation state is a state in which an orientation of the radiation assembly relative to a zero-slope vertical axis satisfies the following condition: an absolute value of an angular difference between the first central axis of the radiation assembly and the zero-slope vertical axis is less than or equal to a first predetermined threshold; and
the unsafe orientation state is a state in which the orientation of the radiation assembly relative to the zero-slope vertical axis satisfies the following condition: the absolute value of the angular difference between the first central axis of the radiation assembly and the zero-slope vertical axis is greater than the first predetermined threshold.

11. The liquid storage system of claim 10, wherein:
the second safety assembly includes a gravity-related sensor, the gravity-related sensor configured to detect the orientation of the radiation assembly relative to the zero-slope vertical axis.

12. The liquid storage system of claim 1, wherein:
the second safety assembly includes a pressure-related sensor, the pressure-related sensor configured to detect when a liquid housed in the main storage section exerts a pressure greater than a first threshold value onto the pressure-related sensor.

13. The liquid storage system of claim 1, wherein the control processor is further configured to:
control the radiation assembly to not emit the UV radiation when the first safety assembly determines that the liquid storage system is in the secured state and the second safety assembly determines that the secondary assembly is in the unsafe orientation state;
control the radiation assembly to not emit the UV radiation when the first safety assembly determines that the liquid storage system is in the unsecured state and the second safety assembly determines that the secondary assembly is in the safe orientation state; and
control the radiation assembly to not emit the UV radiation when the first safety assembly determines that the liquid storage system is in the unsecured state and the second safety assembly determines that the secondary assembly is in the unsafe orientation state.

14. A liquid storage system, the liquid storage system comprising:
a main assembly, the main assembly having:
  a main opening;
  a main storage section, the main storage section formed by a surrounding side wall and a bottom wall opposite to the main opening, the main storage section configured to receive a liquid via the main opening; and a main securing portion; and a secondary assembly, the secondary assembly configured to secure to and unsecure from the main assembly, the secondary assembly including:

a secondary securing portion, the secondary securing portion configured to cooperate with the main securing portion to transition the liquid storage system between a secured state and an unsecured state, the secured state being a state in which the secondary securing portion and the main securing portion are secured together to create a secure hermetical seal of the main opening, the unsecured state being a state in which the secondary securing portion and the main securing portion are not secured together to create a secure hermetical seal of the main opening;

a radiation assembly, the radiation assembly configured to emit UV radiation, the radiation assembly formed symmetrically relative to a first central axis; and a control assembly, the control assembly including:

a first safety assembly, the first safety assembly configured to determine whether the liquid storage system is in the secured state or the unsecured state;

a second safety assembly, the second safety assembly configured to determine whether the secondary assembly is in:

a safe orientation, the safe orientation state being a state in which an orientation of the radiation assembly relative to a zero-slope vertical axis satisfies the following condition: an absolute value of an angular difference between the first central axis of the radiation assembly and the zero-slope vertical axis is less than or equal to a first predetermined threshold; or an unsafe orientation, the unsafe orientation state being a state in which the orientation of the radiation assembly relative to the zero-slope vertical axis satisfies the following condition: the absolute value of the angular difference between the first central axis of the radiation assembly and the zero-slope vertical axis is greater than the first predetermined threshold; and a control processor, the control processor configured to control the radiation assembly to emit the UV radiation when:

the first safety assembly determines that the liquid storage system is in the secured state; and the second safety assembly determines that the secondary assembly is in the safe orientation state.

15. The liquid storage system of claim 14, wherein:
the radiation assembly is configured to emit UV radiation within a conical-shaped region, the conical-shaped region being coaxial with the radiation assembly, the conical-shaped region having an angle of not more than 80 degrees and not less than 40 degrees relative to the first central axis.

16. The liquid storage system of claim 15, wherein:
the conical-shaped region has an angle of not more than 70 degrees and not less than 50 degrees relative to the first central axis.

17. The liquid storage system of claim 15, wherein:
the conical-shaped region has an angle of 60 degrees relative to the first central axis.

18. The liquid storage system of claim 14, wherein:
the radiation assembly includes one or more UV radiation sources;
each of the one or more UV radiation sources are configured to emit UV radiation within a conical-shaped region, each conical-shaped region having a central axis parallel to the first central axis; and
each conical-shaped region has an angle of not more than 80 degrees and not less than 40 degrees relative to the first central axis.

19. The liquid storage system of claim 18, wherein:
each conical-shaped region has an angle of not more than 70 degrees and not less than 50 degrees relative to the first central axis.

20. The liquid storage system of claim 18, wherein:
each conical-shaped region has an angle of 60 degrees relative to the first central axis.

21. The liquid storage system of claim 14, wherein:
the first safety assembly includes a light sensor, the light sensor configured to detect a presence of visible light;
the first safety assembly determines that the liquid storage system is in the secured state when the light sensor does not detect the presence of visible light; and
the first safety assembly determines that the liquid storage system is in the unsecured state when the light sensor detects the presence of visible light.

22. The liquid storage system of claim 14, wherein:
the first safety assembly includes a contact sensor;
the contact sensor is configured to detect whether or not the main securing portion is secured to the secondary securing portion;
the first safety assembly determines that the liquid storage system is in the secured state when the contact sensor detects that the main securing portion is secured to the secondary securing portion; and
the first safety assembly determines that the liquid storage system is in the unsecured state when the contact sensor detects that the main securing portion is not secured to the secondary securing portion.

23. The liquid storage system of claim 14, wherein:
the second safety assembly includes a gravity-related sensor, the gravity-related sensor configured to detect the orientation of the radiation assembly relative to the zero-slope vertical axis.

24. The liquid storage system of claim 14, wherein the control processor is further configured to:
control the radiation assembly to not emit the UV radiation when the first safety assembly determines that the liquid storage system is in the secured state and the second safety assembly determines that the secondary assembly is in the unsafe orientation state;
control the radiation assembly to not emit the UV radiation when the first safety assembly determines that the liquid storage system is in the unsecured state and the second safety assembly determines that the secondary assembly is in the safe orientation state; and
control the radiation assembly to not emit the UV radiation when the first safety assembly determines that the liquid storage system is in the unsecured state and the second safety assembly determines that the secondary assembly is in the unsafe orientation state.

25. A liquid storage system, the liquid storage system comprising:
a main assembly, the main assembly having:
a main opening;
a main storage section, the main storage section formed by a surrounding side wall and a bottom wall opposite to the main opening, the main storage section configured to receive a liquid via the main opening; and
a main securing portion; and
a secondary assembly, the secondary assembly configured to secure to and unsecure from the main assembly, the secondary assembly including:
a secondary securing portion, the secondary securing portion configured to cooperate with the main securing portion to transition the liquid storage system between a secured state and an unsecured state, the secured state being a state in which the secondary securing portion and the main securing portion are secured together to hermetically seal the main opening, the unsecured state being a state in which the secondary securing portion and the main securing portion are not secured together to hermetically seal the main opening;
a radiation assembly, the radiation assembly configured to emit UV radiation, the radiation assembly formed symmetrically relative to a first central axis; and
a control assembly, the control assembly including:
a first safety assembly, the first safety assembly configured to determine whether the liquid storage system is in the secured state or the unsecured state;
a second safety assembly, the second safety assembly configured to determine whether the secondary assembly is in a safe orientation state or an unsafe orientation state; and
a control processor, the control processor configured to:
control the radiation assembly to emit the UV radiation when the first safety assembly determines that the liquid storage system is in the secured state and the second safety assembly determines that the secondary assembly is in the safe orientation state;
control the radiation assembly to not emit the UV radiation when the first safety assembly determines that the liquid storage system is in the secured state and the second safety assembly determines that the secondary assembly is in the unsafe orientation state;
control the radiation assembly to not emit the UV radiation when the first safety assembly determines that the liquid storage system is in the unsecured state and the second safety assembly determines that the secondary assembly is in the safe orientation state; and
control the radiation assembly to not emit the UV radiation when the first safety assembly determines that the liquid storage system is in the unsecured state and the second safety assembly determines that the secondary assembly is in the unsafe orientation state.

26. The liquid storage system of claim 25, wherein:
the radiation assembly is configured to emit UV radiation within a conical-shaped region, the conical-shaped region being coaxial with the radiation assembly, the conical-shaped region having an angle of not more than 80 degrees and not less than 40 degrees relative to the first central axis.

27. The liquid storage system of claim 26, wherein:
the conical-shaped region has an angle of not more than 70 degrees and not less than 50 degrees relative to the first central axis.

28. The liquid storage system of claim 26, wherein:
the conical-shaped region has an angle of 60 degrees relative to the first central axis.

29. The liquid storage system of claim 25, wherein:
the radiation assembly includes one or more UV radiation sources;
each of the one or more UV radiation sources are configured to emit UV radiation within a conical-shaped region, each conical-shaped region having a central axis parallel to the first central axis; and
each conical-shaped region has an angle of not more than 80 degrees and not less than 40 degrees relative to the first central axis.

30. The liquid storage system of claim 29, wherein:
each conical-shaped region has an angle of not more than 70 degrees and not less than 50 degrees relative to the first central axis.

31. The liquid storage system of claim 29, wherein:
each conical-shaped region has an angle of 60 degrees relative to the first central axis.

32. The liquid storage system of claim 25, wherein:
the first safety assembly includes a light sensor, the light sensor configured to detect a presence of visible light;
the first safety assembly determines that the liquid storage system is in the secured state when the light sensor does not detect the presence of visible light; and
the first safety assembly determines that the liquid storage system is in the unsecured state when the light sensor detects the presence of visible light.

33. The liquid storage system of claim 25, wherein:
the first safety assembly includes a contact sensor;
the contact sensor is configured to detect whether or not the main securing portion is secured to the secondary securing portion;
the first safety assembly determines that the liquid storage system is in the secured state when the contact sensor detects that the main securing portion is secured to the secondary securing portion; and
the first safety assembly determines that the liquid storage system is in the unsecured state when the contact sensor detects that the main securing portion is not secured to the secondary securing portion.

34. The liquid storage system of claim 25, wherein:
the safe orientation state is a state in which an orientation of the radiation assembly relative to a zero-slope vertical axis satisfies the following condition: an absolute value of an angular difference between the first central axis of the radiation assembly and the zero-slope vertical axis is less than or equal to a first predetermined threshold; and
the unsafe orientation state is a state in which the orientation of the radiation assembly relative to the zero-slope vertical axis satisfies the following condition: the absolute value of the angular difference between the first central axis of the radiation assembly and the zero-slope vertical axis is greater than the first predetermined threshold.

35. The liquid storage system of claim 34, wherein:
the second safety assembly includes a gravity-related sensor, the gravity-related sensor configured to detect the orientation of the radiation assembly relative to the zero-slope vertical axis.

36. The liquid storage system of claim 25, wherein:
the second safety assembly includes a pressure-related sensor, the pressure-related sensor configured to detect when a liquid housed in the main storage section exerts a pressure greater than a first threshold value onto the pressure-related sensor.

* * * * *